US005621126A

United States Patent [19]
Canich et al.

[11] Patent Number: 5,621,126
[45] Date of Patent: Apr. 15, 1997

[54] MONOCYCLOPENTADIENYL METAL COMPOUNDS FOR ETHYLENE-α-OLEFIN-COPOLYMER PRODUCTION CATALYSTS

[75] Inventors: Jo Ann M. Canich, Webster; Howard W. Turner; Gregory G. Hlatky, both of Houston, all of Tex.

[73] Assignee: Exxon Chemical Patents Inc., Wilmington, Del.

[21] Appl. No.: 138,169

[22] Filed: Oct. 15, 1993

Related U.S. Application Data

[63] Continuation-in-part of Ser. No. 850,751, Mar. 13, 1992, Pat. No. 5,264,405, which is a continuation-in-part of Ser. No. 581,841, Sep. 19, 1990, Pat. No. 5,096,867, which is a continuation-in-part of Ser. No. 533,245, Jun. 4, 1990, Pat. No. 5,055,438, which is a continuation-in-part of Ser. No. 406,945, Sep. 13, 1989, abandoned, Ser. No. 542,236, Jun. 22, 1990, and Ser. No. 938,198, Aug. 28, 1992, abandoned, which is a continuation of Ser. No. 133,480, Dec. 22, 1987, abandoned, which is a continuation-in-part of Ser. No. 8,800, Jan. 30, 1987, abandoned, and a continuation-in-part of Ser. No. 875,165, Apr. 28, 1992, Pat. No. 5,278,119, which is a continuation of Ser. No. 133,052, Dec. 21, 1987, abandoned, which is a continuation-in-part of Ser. No. 11,471, Jan. 30, 1987, abandoned.

[51] Int. Cl.$^6$ .................... C07F 17/00; C07F 7/00
[52] U.S. Cl. .............. 556/9; 502/152; 526/943; 526/160; 556/11; 556/12; 556/52; 556/54; 556/56
[58] Field of Search .................. 556/52, 54, 56, 556/9, 11, 12; 526/943; 502/152

[56] References Cited

U.S. PATENT DOCUMENTS

| | | | |
|---|---|---|---|
| 5,026,798 | 6/1991 | Canich | 526/127 |
| 5,055,438 | 10/1991 | Canich | 502/117 |
| 5,057,475 | 10/1991 | Canich et al. | 502/104 |
| 5,064,802 | 11/1991 | Stevens et al. | 502/155 |
| 5,066,741 | 11/1991 | Campbell, Jr. | 526/171 |
| 5,096,867 | 3/1992 | Canich | 502/103 |
| 5,132,380 | 7/1992 | Stevens et al. | 526/126 |
| 5,168,111 | 12/1992 | Canich | 526/160 |
| 5,189,192 | 2/1993 | LaPointe et al. | 556/11 |
| 5,227,440 | 7/1993 | Canich et al. | 526/129 |
| 5,264,405 | 11/1993 | Canich | 502/103 |
| 5,272,236 | 12/1993 | Lai et al. | 526/348.5 |
| 5,278,272 | 1/1994 | Lai et al. | 526/348.5 |

FOREIGN PATENT DOCUMENTS

| | | |
|---|---|---|
| 416815 | 3/1991 | European Pat. Off. |
| 468651 | 1/1992 | European Pat. Off. |
| 514828 | 11/1992 | European Pat. Off. |
| 520732 | 12/1992 | European Pat. Off. |
| 93/08221 | 4/1993 | WIPO |
| 93/08199 | 4/1993 | WIPO |
| 93/13140 | 7/1993 | WIPO |

OTHER PUBLICATIONS

Chemical Abstracts, vol. 117, Abstract. No. 112121.
Chemical Abstracts, vol. 123, Abstract. No. 199423.
M. Reetz, *Organotitanium Reagents in Organic Synthesis*, pp. 117 and 121 (Springer–Verlay 1986).
Kükenhöhner, "Untersuchungen zur Darstellung Chiraler Organotian (IV)–Verbindungen für Enantioselektire Synthesen" (1983) (unpublished Diplomarbeit, University of Marburg, Germany).
Kükenhöhner, "Organotitan (IV) Agentien: Komplexe Chiraler Chelatliganden und Enantioselektire c–c–Verknüpfungen" (University of Marburg, Germany 1986).

*Primary Examiner*—Porfirio Nazario-Gonzalez

[57] ABSTRACT

Described are certain mono(cyclopentadienyl) Group IV B metal compounds, catalyst systems comprising such mono-(cyclopentadienyl) metal compounds and an activator, and to a process using such catalyst systems for the production of polyolefins, particularly ethylene-α-olefin copolymers having a high molecular weight and high level of α-olefin incorporation.

10 Claims, No Drawings

MONOCYCLOPENTADIENYL METAL COMPOUNDS FOR ETHYLENE-α-OLEFIN-COPOLYMER PRODUCTION CATALYSTS

SPECIFICATION

This application is a continuation-in-part of U.S. Ser. No. 850,751, filed Mar. 13, 1992, now U.S. Pat. No. 5,264,405, which is a continuation-in-part of U.S. Ser. No. 581,841, filed Sep. 19, 1990, now U.S. Pat. No. 5,096,867, which is a continuation-in-part of U.S. Ser. No. 533,245 filed Jun. 4, 1990, now U.S. Pat. No. 5,055,438, which is a continuation-in-part of U.S. Ser. No. 406,945 filed Sep. 13, 1989, now abandoned. This application is also a continuation-in-part of U.S. Ser. No. 542,236 filed Jun. 22, 1990 and is a continuation-in-part of 938,198 filed Aug. 28, 1992 now abandoned which is a continuation of U.S. Ser. No. 133,480, now abandoned, filed Dec. 22, 1987, which is a continuation-in-part of U.S. Ser. No. 008,800, filed Jan. 30, 1987, now abandoned and a continuation-in-part of U.S. Ser. No. 875,165 filed Apr. 28, 1992, now U.S. Pat. No. 5,278,119, which is a continuation of U.S. Ser. No. 133,052, now abandoned, filed Dec. 21, 1987, which is a continuation-in-part of U.S. Ser. No. 011,471, filed Jan. 30, 1987, now abandoned.

FIELD OF THE INVENTION

This invention relates to certain monocyclopentadienyl metal compounds, to a catalyst system comprising a monocyclopentadienyl metal compound and an activator, and to a process using such catalyst system for the production of polyolefins, particularly ethylene-α-olefin copolymers having a high molecular weight and high level of α-olefin incorporation.

This invention relates to the discovery of various catalyst ligand structure affects which are reflected in the activity of the catalyst system and in the physical and chemical properties possessed by a polymer produced with a monocyclopentadienyl catalyst system. Accordingly, various species within the general class of monocyclopentadienyl metal catalysts have been discovered to be vastly superior in terms of the ability of such species to produce ethylene-α-olefin copolymers of high molecular weight with high levels of α-olefin comonomer incorporation and at high levels of catalyst productivity.

BACKGROUND OF THE INVENTION

As is well known, various processes and catalysts exist for homopolymerization or copolymerization of olefins. For many applications it is of primary importance for a polyolefin to have a high weight average molecular weight while having a relatively narrow molecular weight distribution. A high weight average molecular weight, when accompanied by a narrow molecular weight distribution, provides a polyolefin or an ethylene-α-olefin copolymer with high strength properties.

Traditional Ziegler-Natta catalyst systems—a transition metal compound cocatalyzed by an aluminum alkyl—are capable of producing polyolefins having a high molecular weight but a broad molecular weight distribution.

More recently a catalyst system has been developed wherein the transition metal compound has two or more cyclopentadienyl ring ligands—such transition metal compound being referred to as a metallocene—which catalyzes the production of olefin monomers to polyolefins. Accordingly, metallocene compounds of a Group IV B metal, particularly, titanocenes and zirconocenes, have been utilized as the transition metal component in such "metallocene" containing catalyst systems for the production of polyolefins and ethylene-α-olefin copolymers. When such metallocenes are cocatalyzed with an aluminum alkyl—as is the case with a traditional type Ziegler-Natta catalyst system—the catalytic activity of such metallocene catalyst system is generally too low to be of any commercial interest.

It has since become known that such metallocenes may be cocatalyzed with an alumoxane—rather than an aluminum alkyl—to provide a metallocene catalyst system of high activity for the production of polyolefins.

The zirconium metallocene species, as cocatalyzed or activated with an alumoxane, are commonly more active than their hafnium or titanium analogues for the polymerization of ethylene alone or together with an α-olefin comonomer. When employed in a non-supported form—i.e., as a homogeneous or soluble catalyst system—to obtain a satisfactory rate of productivity even with the most active zirconocene species typically requires the use of a quantity of alumoxane activator sufficient to provide an aluminum atom to transition metal atom ratio (Al:TM) of at least greater than 1000:1; often greater than 5000:1, and frequently on the order of 10,000:1. Such quantities of alumoxane impart to a polymer produced with such catalyst system an undesirable content of catalyst metal residue, i.e., an undesirable "ash" content (the nonvolatile metal content). In high pressure polymerization procedures using soluble catalyst systems wherein the reactor pressure exceeds about 500 bar only the zirconocene or hafnocene species may be used. Titanocene species are generally unstable at such high pressure unless deposited upon a catalyst support.

A wide variety of Group IV B transition metal compounds have been named as possible candidates for an alumoxane cocatalyzed catalyst system. Although bis(cyclopentadienyl) Group IV B transition metal compounds have been the most preferred and heavily investigated for use in alumoxane activated catalyst systems for polyolefin production, suggestions have appeared that mono and tris(cyclopentadienyl) transition metal compounds may also be useful. See, for example U.S. Pat. Nos. 4,522,982; 4,530,914 and 4,701,431. Such mono(cyclopentadienyl) transition metal compounds as have heretofore been suggested as candidates for an alumoxane activated catalyst system are mono(cyclopentadienyl) transition metal trihalides and trialkyls.

International Publication No. WO 87/03887 describes the use of a composition comprising a transition metal coordinated to at least one cyclopentadienyl and at least one heteroatom ligand as a transition metal component for use in an alumoxane activated catalyst system for α-olefin polymerization. The composition is broadly defined as a transition metal, preferably of Group IV B of the Periodic Table, which is coordinated with at least one cyclopentadienyl ligand and one to three heteroatom ligands, the balance of the transition metal coordination requirement being satisfied with cyclopentadienyl or hydrocarbyl ligands. Catalyst systems described by this reference are illustrated solely with reference to transition metal compounds which are metallocenes, i.e., bis(cyclopentadienyl) Group IV B transition metal compounds.

At the Third Chemical Congress of North American held in Toronto, Canada in June 1988, John Bercaw reported upon efforts to use a compound of a Group III B transition metal coordinated to a single cyclopentadienyl heteroatom bridged ligand as a catalyst system for the polymerization of olefins. Although some catalytic activity was observed under the conditions employed, the degree of activity and the properties observed in the resulting polymer product were discouraging of a belief that such mono(cyclopentadienyl) transition metal compound could be usefully employed for commercial polymerization processes.

Although the metallocene/alumoxane catalyst system constituted an improvement relative to a traditional Ziegler-Natta catalyst system, a need existed for discovering catalyst systems that permit the production of higher molecular weight polyolefins and desirably with a narrow molecular weight distribution. Further desired was a catalyst which, within reasonable ranges of ethylene to α-olefin monomer ratios, will catalyze the incorporation of higher contents of α-olefin comonomers in the production of ethylene-α-olefins copolymers.

EPO 416,815 discloses certain mono(cyclopentadienyl) metal compounds which are activated with an alumoxane cocatalyst. U.S. Pat. No. 5,064,802 discloses certain mono-(cyclopentadienyl) metal compounds which are activated with a non-coordinating compatible anion of a Bronsted acid salt.

SUMMARY OF THE INVENTION

The present invention is a catalyst system including a mono(cyclopentadienyl) metal compound and an activator component. The catalyst system is highly productive for polymerizing ethylene and α-olefins to produce a high molecular weight ethylene-α-olefin copolymer having a high content of α-olefin. More particularly, the present invention relates to certain mono(cyclopentadienyl) metal compounds which include an amido moiety having an aliphatic or alicyclic hydrocarbyl group covalently bonded thereto through a primary or secondary carbon atom.

DETAILED DESCRIPTION OF THE INVENTION

This invention comprises the discovery of a subgenus of mono(cyclopentadienyl) metal compounds which, by reason of the presence therein of ligands of a particular nature, provide a catalyst of greatly improved performance characteristics compared to known members of the genus of mono(cyclopentadienyl) metal compounds. The mono(cyclopentadienyl) metal compounds of the present invention are represented by the formula:

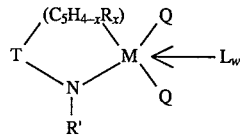

Formula I wherein: M is Zr, Hf or Ti;

($C_5H_{4-x}R_x$) is a cyclopentadienyl ring which is substituted with from zero to four substituent groups R, "x" is 0, 1, 2, 3, or 4 denoting the degree of substitution, and each substituent group R is, independently, a radical selected from a group consisting of $C_1$–$C_{20}$ hydrocarbyl radicals, substituted $C_1$–$C_{20}$ hydrocarbyl radicals wherein one or more hydrogen atoms is replaced by a halogen radical, an amido radical, a phosphido radical, and alkoxy radical or any other radical containing a Lewis acidic or basic functionality, $C_1$–$C_{20}$ hydrocarbyl-substituted metalloid radicals wherein the metalloid is selected from the Group IV A of the Periodic Table of Elements, halogen radicals, amido radicals, phosphido radicals, alkoxy radicals, alkylborido radicals or any other radical containing Lewis acidic or basic functionality; or ($C_5H_{4-x}R_x$) is a cyclopentadienyl ring in which at least two adjacent R-groups are joined forming a $C_4$–$C_{20}$ ring to give a saturated or unsaturated polycyclic cyclopentadienyl ligand such as indenyl, tetrahydroindenyl, fluorenyl or octahydrofluorenyl;

R' is a radical selected from $C_1$–$C_{20}$ aliphatic and alicyclic hydrocarbyl radicals wherein one or more hydrogen atoms may be replaced by radicals selected from halogen, amido, phosphido, alkoxy or any other radical containing a Lewis acidic or basic functionality, with the proviso that R' is covalently bonded to the nitrogen atom through a 1° or 2° carbon atom;

each Q is independently a halide, hydride, or substituted or unsubstituted $C_1$–$C_{20}$ hydrocarbyl, alkoxide, aryloxide, amide, phosphide or both Q together may be an alkylidene or a cyclometallated hydrocarbyl or any other divalent anionic chelating ligand, with the proviso that where any Q is a hydrocarbyl such Q is not a substituted or unsubstituted cyclopentadienyl radical,;

T is a covalent bridging group containing a Group IV A or V A element such as, but not limited to, a dialkyl, alkylaryl or diaryl silicon or germanium radical, alkyl or aryl phosphine or amine radical, or a substituted or unsubstituted hydrocarbyl radical such as methylene, ethylene and the like which may be substituted with substituents selected from alkyl and aryl radicals having from 1 to 20 carbon atoms;

L is a neutral Lewis base such as diethylether, tetraethylammonium chloride, tetrahydrofuran, dimethylaniline, aniline, trimethylphosphine, n-butylamine, and the like; and "w" is a number from 0 to 3.

L can also be a second transition metal compound of the same type such that the two metal centers M and M' are bridged by Q and Q', wherein M' has the same meaning as M and Q' has the same meaning as Q. Such dimeric compounds are represented by the formula:

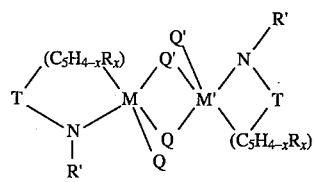

Formula II

A preferred class of compounds of the present invention are represented by the formula:

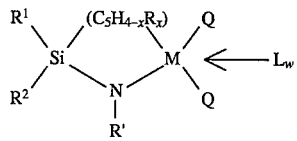

Formula III wherein:

M represents Ti, Hf or Zr;

($C_5H_{4-x}R_x$) is as defined above with respect to Formula I;

each of $R^1$ and $R^2$ are independently selected from $C_1$–$C_{20}$ hydrocarbyl radicals;

each Q is independently selected from halide, hydride, substituted or unsubstituted $C_1$–$C_{20}$ hydrocarbyl radical, alkoxide, amide and phosphide radicals with the proviso that Q is not a substituted or unsubstituted cyclopentadienyl radical;

R' is selected from $C_1$–$C_{20}$ aliphatic and alicyclic hydrocarbyl radicals with the proviso that R' is covalently bonded to the nitrogen atom through a 1° or 2° carbon atom;

$L_w$ is as defined above, and x is an integer of from 0 to 4.

A more preferred class of compounds of the present invention are those compounds represented by Formula III wherein M is Ti; wherein R, R', Q, and $L_w$ are as defined above; and $R^1$ and $R^2$ are selected from alkyl and aryl radicals having from 1 to 20 carbon atoms.

A most preferred class of compounds are represented by the above Formula III wherein R' is selected from alicyclic radicals particularly those having from 6 to 12 carbon atoms.

Examples of specific compounds within the classes of compounds defined by Formula III include:

dimethylsilyl(tetramethylcyclopentadienyl)-(cyclopropylamido)titanium dimethyl;

dimethylsilyl(tetramethylcyclopentadienyl)-(cyclobutylamido)titanium dimethyl;

dimethylsilyl(tetramethylcyclopentadienyl)-(cyclopentylamido)titanium dimethyl;

dimethylsilyl(tetramethylcyclopentadienyl)-(cyclohexylamido)titanium dimethyl;

dimethylsilyl(tetramethylcyclopentadienyl)-(cycloheptylamido)titanium dimethyl;

dimethylsilyl(tetramethylcyclopentadienyl)-(cyclooctylamido)titanium dimethyl;

dimethylsilyl(tetramethylcyclopentadienyl)-(cyclononylamido)titanium dimethyl;

dimethylsilyl(tetramethylcyclopentadienyl)-(cyclodecylamido)titanium dimethyl;

dimethylsilyl(tetramethylcyclopentadienyl)-(cycloundecylamido)titanium dimethyl;

dimethylsilyl(tetramethylcyclopentadienyl)-(cyclododecylamido)titanium dimethyl;

dimethylsilyl(tetramethylcyclopentadienyl)-(sec-butylamido)titanium dimethyl;

dimethylsilyl(tetramethylcyclopentadienyl)-(n-octylamido)titanium dimethyl;

dimethylsilyl(tetramethylcyclopentadienyl)-(n-decylamido)titanium dimethyl;

dimethylsilyl(tetramethylcyclopentadienyl)-(n-octadecylamido)titanium dimethyl;

methylphenylsilyl(tetramethylcyclopentadienyl)-(cyclopropylamido)titanium dimethyl;

methylphenylsilyl(tetramethylcyclopentadienyl)-(cyclobutylamido)titanium dimethyl;

methylphenylsilyl(tetramethylcyclopentadienyl)-(cyclopentylamido)titanium dimethyl;

methylphenylsilyl(tetramethylcyclopentadienyl)-(cyclohexylamido)titanium dimethyl;

methylphenylsilyl(tetramethylcyclopentadienyl)-(cycloheptylamido)titanium dimethyl;

methylphenylsilyl(tetramethylcyclopentadienyl)-(cyclooctylamido)titanium dimethyl;

methylphenylsilyl(tetramethylcyclopentadienyl)-(cyclononylamido)titanium dimethyl;

methylphenylsilyl(tetramethylcyclopentadienyl)-(cyclodecylamido)titanium dimethyl;

methylphenylsilyl(tetramethylcyclopentadienyl)-(cycloundecylamido)titanium dimethyl;

methylphenylsilyl(tetramethylcyclopentadienyl)-(cyclododecylamido)titanium dimethyl;

methylphenylsilyl(tetramethylcyclopentadienyl)-(sec-butylamido)titanium dimethyl;

methylphenylsilyl(tetramethylcyclopentadienyl)-(n-octylamido)titanium dimethyl;

methylphenylsilyl(tetramethylcyclopentadienyl)-(n-decylamido)titanium dimethyl;

methylphenylsilyl(tetramethylcyclopentadienyl)-(n-octadecylamido)titanium dimethyl;

diphenylsilyl(tetramethylcyclopentadienyl)(cyclopropylamido)titanium dimethyl;

diphenylsilyl(tetramethylcyclopentadienyl)-(cyclobutylamido)titanium dimethyl;

diphenylsilyl(tetramethylcyclopentadienyl)-(cyclopentylamido)titanium dimethyl;

diphenylsilyl(tetramethylcyclopentadienyl)-(cyclohexylamido)titanium dimethyl;

diphenylsilyl(tetramethylcyclopentadienyl)-(cycloheptylamido)titanium dimethyl;

diphenylsilyl(tetramethylcyclopentadienyl)-(cyclooctylamido)titanium dimethyl;

diphenylsilyl(tetramethylcyclopentadienyl)-(cyclononylamido)titanium dimethyl;

diphenylsilyl(tetramethylcyclopentadienyl)-(cyclodecylamido)titanium dimethyl;

diphenylsilyl(tetramethylcyclopentadienyl)-(cycloundecylamido)titanium dimethyl;

diphenylsilyl(tetramethylcyclopentadienyl)-(cyclododecylamido)titanium dimethyl;

diphenylsilyl(tetramethylcyclopentadienyl)-(sec-butylamido)titanium dimethyl;

diphenylsilyl(tetramethylcyclopentadienyl)-(n-octylamido)titanium dimethyl;

diphenylsilyl(tetramethylcyclopentadienyl)-(n-decylamido)titanium dimethyl;

diphenylsilyl(tetramethylcyclopentadienyl)-(n-octadecylamido)titanium dimethyl;

dimethylsilyl(tetramethylcyclopentadienyl)-(cyclopropylamido)titanium diphenyl;

dimethylsilyl(tetramethylcyclopentadienyl)-(cyclobutylamido)titanium diphenyl;

dimethylsilyl(tetramethylcyclopentadienyl)-(cyclopentylamido)titanium diphenyl;

dimethylsilyl(tetramethylcyclopentadienyl)-(cyclohexylamido)titanium diphenyl;

dimethylsilyl(tetramethylcyclopentadienyl)-(cycloheptylamido)titanium diphenyl;

dimethylsilyl(tetramethylcyclopentadienyl)-(cyclooctylamido)titanium diphenyl;

dimethylsilyl(tetramethylcyclopentadienyl)-(cyclononylamido)titanium diphenyl;

dimethylsilyl(tetramethylcyclopentadienyl)-(cyclodecylamido)titanium diphenyl;

dimethylsilyl(tetramethylcyclopentadienyl)-(cycloundecylamido)titanium diphenyl;

dimethylsilyl(tetramethylcyclopentadienyl)-(cyclododecylamido)titanium diphenyl;

dimethylsilyl(tetramethylcyclopentadienyl)-(sec-butylamido)titanium diphenyl;

dimethylsilyl(tetramethylcyclopentadienyl)-(n-octylamido)titanium diphenyl;

dimethylsilyl(tetramethylcyclopentadienyl)-(n-decylamido)titanium diphenyl;
dimethylsilyl(tetramethylcyclopentadienyl)-(n-octadecylamido)titanium diphenyl;
methylphenylsilyl(tetramethylcyclopentadienyl)-(cyclopropylamido)titanium diphenyl;
methylphenylsilyl(tetramethylcyclopentadienyl)-(cyclobutylamido)titanium diphenyl;
methylphenylsilyl(tetramethylcyclopentadienyl)-(cyclopentylamido)titanium diphenyl;
methylphenylsilyl(tetramethylcyclopentadienyl)-(cyclohexylamido)titanium diphenyl;
methylphenylsilyl(tetramethylcyclopentadienyl)-(cycloheptylamido)titanium diphenyl;
methylphenylsilyl(tetramethylcyclopentadienyl)-(cyclooctylamido)titanium diphenyl;
methylphenylsilyl(tetramethylcyclopentadienyl)-(cyclononylamido)titanium diphenyl;
methylphenylsilyl(tetramethylcyclopentadienyl)-(cyclodecylamido)titanium diphenyl;
methylphenylsilyl(tetramethylcyclopentadienyl)-(cycloundecylamido)titanium diphenyl;
methylphenylsilyl(tetramethylcyclopentadienyl)(cyclododecylamido)titanium diphenyl;
methylphenylsilyl(tetramethylcyclopentadienyl)-(sec-butylamido)titanium diphenyl;
methylphenylsilyl(tetramethylcyclopentadienyl)-(n-octylamido)titanium diphenyl;
methylphenylsilyl(tetramethylcyclopentadienyl)-(n-decylamido)titanium diphenyl;
methylphenylsilyl(tetramethylcyclopentadienyl)-(n-octadecylamido)titanium diphenyl;
diphenylsilyl(tetramethylcyclopentadienyl)-(cyclopropylamido)titanium diphenyl;
diphenylsilyl(tetramethylcyclopentadienyl)-(cyclobutylamido)titanium diphenyl;
diphenylsilyl(tetramethylcyclopentadienyl)-(cyclopentylamido)titanium diphenyl;
diphenylsilyl(tetramethylcyclopentadienyl)-(cyclohexylamido)titanium diphenyl;
diphenylsilyl(tetramethylcyclopentadienyl)-(cycloheptylamido)titanium diphenyl;
diphenylsilyl(tetramethylcyclopentadienyl)-(cyclooctylamido)titanium diphenyl;
diphenylsilyl(tetramethylcyclopentadienyl)-(cyclononylamido)titanium diphenyl;
diphenylsilyl(tetramethylcyclopentadienyl)-(cyclodecylamido)titanium diphenyl;
diphenylsilyl(tetramethylcyclopentadienyl)-(cycloundecylamido)titanium diphenyl;
diphenylsilyl(tetramethylcyclopentadienyl)-(cyclododecylamido)titanium diphenyl;
diphenylsilyl(tetramethylcyclopentadienyl)-(sec-butylamido)titanium diphenyl;
diphenylsilyl(tetramethylcyclopentadienyl)-(n-octylamido)titanium diphenyl;
diphenylsilyl(tetramethylcyclopentadienyl)-(n-decylamido)titanium diphenyl;
diphenylsilyl(tetramethylcyclopentadienyl)-(n-octadecylamido)titanium diphenyl;
dimethylsilyl(tetramethylcyclopentadienyl)-(cyclopropylamido)hafnium dimethyl;
dimethylsilyl(tetramethylcyclopentadienyl)-(cyclobutylamido)hafnium dimethyl;
dimethylsilyl(tetramethylcyclopentadienyl)-(cyclopentylamido)hafnium dimethyl;
dimethylsilyl(tetramethylcyclopentadienyl)-(cyclohexylamido)hafnium dimethyl;
dimethylsilyl(tetramethylcyclopentadienyl)-(cycloheptylamido)hafnium dimethyl;
dimethylsilyl(tetramethylcyclopentadienyl)-(cyclooctylamido)hafnium dimethyl;
dimethylsilyl(tetramethylcyclopentadienyl)-(cyclononylamido)hafnium dimethyl;
dimethylsilyl(tetramethylcyclopentadienyl)-(cyclodecylamido)hafnium dimethyl;
dimethylsilyl(tetramethylcyclopentadienyl)-(cycloundecylamido)hafnium dimethyl;
dimethylsilyl(tetramethylcyclopentadienyl)-(cyclododecylamido)hafnium dimethyl;
dimethylsilyl(tetramethylcyclopentadienyl)-(sec-butylamido)hafnium dimethyl;
dimethylsilyl(tetramethylcyclopentadienyl)-(n-octylamido)hafnium dimethyl;
dimethylsilyl(tetramethylcyclopentadienyl)-(n-decylamido)hafnium dimethyl;
dimethylsilyl(tetramethylcyclopentadienyl)-(n-octadecylamido)hafnium dimethyl;
methylphenylsilyl(tetramethylcyclopentadienyl)-(cyclopropylamido)hafnium dimethyl;
methylphenylsilyl(tetramethylcyclopentadienyl)-(cyclobutylamido)hafnium dimethyl;
methylphenylsilyl(tetramethylcyclopentadienyl)-(cyclopentylamido)hafnium dimethyl;
methylphenylsilyl(tetramethylcyclopentadienyl)-(cyclohexylamido)hafnium dimethyl;
methylphenylsilyl(tetramethylcyclopentadienyl)-(cycloheptylamido)hafnium dimethyl;
methylphenylsilyl(tetramethylcyclopentadienyl)-(cyclooctylamido)hafnium dimethyl;
methylphenylsilyl(tetramethylcyclopentadienyl)-(cyclononylamido)hafnium dimethyl;
methylphenylsilyl(tetramethylcyclopentadienyl)-(cyclodecylamido)hafnium dimethyl;
methylphenylsilyl(tetramethylcyclopentadienyl)-(cycloundecylamido)hafnium dimethyl;
methylphenylsilyl(tetramethylcyclopentadienyl)-(cyclododecylamido)hafnium dimethyl;
methylphenylsilyl(tetramethylcyclopentadienyl)-(sec-butylamido)hafnium dimethyl;
methylphenylsilyl(tetramethylcyclopentadienyl)-(n-octylamido)hafnium dimethyl;
methylphenylsilyl(tetramethylcyclopentadienyl)-(n-decylamido)hafnium dimethyl;
methylphenylsilyl(tetramethylcyclopentadienyl)-(n-octadecylamido)hafnium dimethyl;
diphenylsilyl(tetramethylcyclopentadienyl)-(cyclopropylamido)hafnium dimethyl;
diphenylsilyl(tetramethylcyclopentadienyl)-(cyclobutylamido)hafnium dimethyl;
diphenylsilyl(tetramethylcyclopentadienyl)-(cyclopentylamido)hafnium dimethyl;
diphenylsilyl(tetramethylcyclopentadienyl)-(cyclohexylamido)hafnium dimethyl;

diphenylsilyl(tetramethylcyclopentadienyl)-(cycloheptylamido)hafnium dimethyl;
diphenylsilyl(tetramethylcyclopentadienyl)-(cyclooctylamido)hafnium dimethyl;
diphenylsilyl(tetramethylcyclopentadienyl)-(cyclononylamido)hafnium dimethyl;
diphenylsilyl(tetramethylcyclopentadienyl)-(cyclodecylamido)hafnium dimethyl;
diphenylsilyl(tetramethylcyclopentadienyl)-(cycloundecylamido)hafnium dimethyl;
diphenylsilyl(tetramethylcyclopentadienyl)-(cyclododecylamido)hafnium dimethyl;
diphenylsilyl(tetramethylcyclopentadienyl)-(sec-butylamido)hafnium dimethyl;
diphenylsilyl(tetramethylcyclopentadienyl)-(n-octylamido)hafnium dimethyl;
diphenylsilyl(tetramethylcyclopentadienyl)-(n-decylamido)hafnium dimethyl;
diphenylsilyl(tetramethylcyclopentadienyl)-(n-octadecylamido)hafnium dimethyl;
dimethylsilyl(tetramethylcyclopentadienyl)-(cyclopropylamido)hafnium diphenyl;
dimethylsilyl(tetramethylcyclopentadienyl)-(cyclobutylamido)hafnium diphenyl;
dimethylsilyl(tetramethylcyclopentadienyl)-(cyclopentylamido)hafnium diphenyl;
dimethylsilyl(tetramethylcyclopentadienyl)-(cyclohexylamido)hafnium diphenyl;
dimethylsilyl(tetramethylcyclopentadienyl)-(cycloheptylamido)hafnium diphenyl;
dimethylsilyl(tetramethylcyclopentadienyl)-(cyclooctylamido)hafnium diphenyl;
dimethylsilyl(tetramethylcyclopentadienyl)-(cyclononylamido)hafnium diphenyl;
dimethylsilyl(tetramethylcyclopentadienyl)-(cyclodecylamido)hafnium diphenyl;
dimethylsilyl(tetramethylcyclopentadienyl)-(cycloundecylamido)hafnium diphenyl;
dimethylsilyl(tetramethylcyclopentadienyl)-(cyclododecylamido)hafnium diphenyl;
dimethylsilyl(tetramethylcyclopentadienyl)-(sec-butylamido)hafnium diphenyl;
dimethylsilyl(tetramethylcyclopentadienyl)-(n-octylamido)hafnium diphenyl;
dimethylsilyl(tetramethylcyclopentadienyl)-(n-decylamido)hafnium diphenyl;
dimethylsilyl(tetramethylcyclopentadienyl)-(n-octadecylamido)hafnium diphenyl;
methylphenylsilyl(tetramethylcyclopentadienyl)-(cyclopropylamido)hafnium diphenyl;
methylphenylsilyl(tetramethylcyclopentadienyl)-(cyclobutylamido)hafnium diphenyl;
methylphenylsilyl(tetramethylcyclopentadienyl)-(cyclopentylamido)hafnium diphenyl;
methylphenylsilyl(tetramethylcyclopentadienyl)-(cyclohexylamido)hafnium diphenyl;
methylphenylsilyl(tetramethylcyclopentadienyl)-(cycloheptylamido)hafnium diphenyl;
methylphenylsilyl(tetramethylcyclopentadienyl)-(cyclooctylamido)hafnium diphenyl;
methylphenylsilyl(tetramethylcyclopentadienyl)-(cyclononylamido)hafnium diphenyl;
methylphenylsilyl(tetramethylcyclopentadienyl)-(cyclodecylamido)hafnium diphenyl;
methylphenylsilyl(tetramethylcyclopentadienyl)-(cycloundecylamido)hafnium diphenyl;
methylphenylsilyl(tetramethylcyclopentadienyl)-(cyclododecylamido)hafnium diphenyl;
methylphenylsilyl(tetramethylcyclopentadienyl)-(sec-butylamido)hafnium diphenyl;
methylphenylsilyl(tetramethylcyclopentadienyl)-(n-octylamido)hafnium diphenyl;
methylphenylsilyl(tetramethylcyclopentadienyl)-(n-decylamido)hafnium diphenyl;
methylphenylsilyl(tetramethylcyclopentadienyl)-(n-octadecylamido)hafnium diphenyl;
diphenylsilyl(tetramethylcyclopentadienyl)-(cyclopropylamido)hafnium diphenyl;
diphenylsilyl(tetramethylcyclopentadienyl)-(cyclobutylamido)hafnium diphenyl;
diphenylsilyl(tetramethylcyclopentadienyl)-(cyclopentylamido)hafnium diphenyl;
diphenylsilyl(tetramethylcyclopentadienyl)-(cyclohexylamido)hafnium diphenyl;
diphenylsilyl(tetramethylcyclopentadienyl)-(cycloheptylamido)hafnium diphenyl;
diphenylsilyl(tetramethylcyclopentadienyl)-(cyclooctylamido)hafnium diphenyl;
diphenylsilyl(tetramethylcyclopentadienyl)-(cyclononylamido)hafnium diphenyl;
diphenylsilyl(tetramethylcyclopentadienyl)-(cyclodecylamido)hafnium diphenyl;
diphenylsilyl(tetramethylcyclopentadienyl)-(cycloundecylamido)hafnium diphenyl;
diphenylsilyl(tetramethylcyclopentadienyl)-(cyclododecylamido)hafnium diphenyl;
diphenylsilyl(tetramethylcyclopentadienyl)-(sec-butylamido)hafnium diphenyl;
diphenylsilyl(tetramethylcyclopentadienyl)-(n-octylamido)hafnium diphenyl;
diphenylsilyl(tetramethylcyclopentadienyl)-(n-decylamido)hafnium diphenyl;
diphenylsilyl(tetramethylcyclopentadienyl)-(n-octadecylamido)hafnium diphenyl;
dimethylsilyl(tetramethylcyclopentadienyl)-(cyclopropylamido)zirconium dimethyl;
dimethylsilyl(tetramethylcyclopentadienyl)-(cyclobutylamido)zirconium dimethyl;
dimethylsilyl(tetramethylcyclopentadienyl)-(cyclopentylamido)zirconium dimethyl;
dimethylsilyl(tetramethylcyclopentadienyl)-(cyclohexylamido)zirconium dimethyl;
dimethylsilyl(tetramethylcyclopentadienyl)-(cycloheptylamido)zirconium dimethyl;
dimethylsilyl(tetramethylcyclopentadienyl)-(cyclooctylamido)zirconium dimethyl;
dimethylsilyl(tetramethylcyclopentadienyl)-(cyclononylamido)zirconium dimethyl;
dimethylsilyl(tetramethylcyclopentadienyl)-(cyclodecylamido)zirconium dimethyl;
dimethylsilyl(tetramethylcyclopentadienyl)-(cycloundecylamido)zirconium dimethyl;
dimethylsilyl(tetramethylcyclopentadienyl)-(cyclododecylamido)zirconium dimethyl;

dimethylsilyl(tetramethylcyclopentadienyl)-(sec-butylamido)zirconium dimethyl;
dimethylsilyl(tetramethylcyclopentadienyl)-(n-octylamido)zirconium dimethyl;
dimethylsilyl(tetramethylcyclopentadienyl)-(n-decylamido)zirconium dimethyl;
dimethylsilyl(tetramethylcyclopentadienyl)-(n-octadecylamido)zirconium dimethyl;
methylphenylsilyl(tetramethylcyclopentadienyl)-(cyclopropylamido)zirconium dimethyl;
methylphenylsilyl(tetramethylcyclopentadienyl)-(cyclobutylamido)zirconium dimethyl;
methylphenylsilyl(tetramethylcyclopentadienyl)-(cyclopentylamido)zirconium dimethyl;
methylphenylsilyl(tetramethylcyclopentadienyl)-(cyclohexylamido)zirconium dimethyl;
methylphenylsilyl(tetramethylcyclopentadienyl)-(cycloheptylamido)zirconium dimethyl;
methylphenylsilyl(tetramethylcyclopentadienyl)-(cyclooctylamido)zirconium dimethyl;
methylphenylsilyl(tetramethylcyclopentadienyl)-(cyclononylamido)zirconium dimethyl;
methylphenylsilyl(tetramethylcyclopentadienyl)-(cyclodecylamido)zirconium dimethyl;
methylphenylsilyl(tetramethylcyclopentadienyl)-(cycloundecylamido)zirconium dimethyl;
methylphenylsilyl(tetramethylcyclopentadienyl)-(cyclododecylamido)zirconium dimethyl;
methylphenylsilyl(tetramethylcyclopentadienyl)-(sec-butylamido)zirconium dimethyl;
methylphenylsilyl(tetramethylcyclopentadienyl)-(n-octylamido)zirconium dimethyl;
methylphenylsilyl(tetramethylcyclopentadienyl)-(n-decylamido)zirconium dimethyl;
methylphenylsilyl(tetramethylcyclopentadienyl)-(n-octadecylamido)zirconium dimethyl;
diphenylsilyl(tetramethylcyclopentadienyl)-(cyclopropylamido)zirconium dimethyl;
diphenylsilyl(tetramethylcyclopentadienyl)-(cyclobutylamido)zirconium dimethyl;
diphenylsilyl(tetramethylcyclopentadienyl)-(cyclopentylamido)zirconium dimethyl;
diphenylsilyl(tetramethylcyclopentadienyl)-(cyclohexylamido)zirconium dimethyl;
diphenylsilyl(tetramethylcyclopentadienyl)-(cycloheptylamido)zirconium dimethyl;
diphenylsilyl(tetramethylcyclopentadienyl)-(cyclooctylamido)zirconium dimethyl;
diphenylsilyl(tetramethylcyclopentadienyl)-(cyclononylamido)zirconium dimethyl;
diphenylsilyl(tetramethylcyclopentadienyl)-(cyclodecylamido)zirconium dimethyl;
diphenylsilyl(tetramethylcyclopentadienyl)-(cycloundecylamido)zirconium dimethyl;
diphenylsilyl(tetramethylcyclopentadienyl)-(cyclododecylamido)zirconium dimethyl;
diphenylsilyl(tetramethylcyclopentadienyl)-(sec-butylamido)zirconium dimethyl;
diphenylsilyl(tetramethylcyclopentadienyl)-(n-octylamido)zirconium dimethyl;
diphenylsilyl(tetramethylcyclopentadienyl)-(n-decylamido)zirconium dimethyl;
diphenylsilyl(tetramethylcyclopentadienyl)-(n-octadecylamido)zirconium dimethyl;
dimethylsilyl(tetramethylcyclopentadienyl)-(cyclopropylamido)zirconium diphenyl;
dimethylsilyl(tetramethylcyclopentadienyl)-(cyclobutylamido)zirconium diphenyl;
dimethylsilyl(tetramethylcyclopentadienyl)-(cyclopentylamido)zirconium diphenyl;
dimethylsilyl(tetramethylcyclopentadienyl)-(cyclohexylamido)zirconium diphenyl;
dimethylsilyl(tetramethylcyclopentadienyl)-(cycloheptylamido)zirconium diphenyl;
dimethylsilyl(tetramethylcyclopentadienyl)-(cyclooctylamido)zirconium diphenyl;
dimethylsilyl(tetramethylcyclopentadienyl)-(cyclononylamido)zirconium diphenyl;
dimethylsilyl(tetramethylcyclopentadienyl)-(cyclodecylamido)zirconium diphenyl;
dimethylsilyl(tetramethylcyclopentadienyl)-(cycloundecylamido)zirconium diphenyl;
dimethylsilyl(tetramethylcyclopentadienyl)-(cyclododecylamido)zirconium diphenyl;
dimethylsilyl(tetramethylcyclopentadienyl)-(sec-butylamido)zirconium diphenyl;
dimethylsilyl(tetramethylcyclopentadienyl)-(n-octylamido)zirconium diphenyl;
dimethylsilyl(tetramethylcyclopentadienyl)-(n-decylamido)zirconium diphenyl;
dimethylsilyl(tetramethylcyclopentadienyl)-(n-octadecylamido)zirconium diphenyl;
methylphenylsilyl(tetramethylcyclopentadienyl)-(cyclopropylamido)zirconium diphenyl;
methylphenylsilyl(tetramethylcyclopentadienyl)-(cyclobutylamido)zirconium diphenyl;
methylphenylsilyl(tetramethylcyclopentadienyl)-(cyclopentylamido)zirconium diphenyl;
methylphenylsilyl(tetramethylcyclopentadienyl)-(cyclohexylamido)zirconium diphenyl;
methylphenylsilyl(tetramethylcyclopentadienyl)-(cycloheptylamido)zirconium diphenyl;
methylphenylsilyl(tetramethylcyclopentadienyl)-(cyclooctylamido)zirconium diphenyl;
methylphenylsilyl(tetramethylcyclopentadienyl)-(cyclononylamido)zirconium diphenyl;
methylphenylsilyl(tetramethylcyclopentadienyl)-(cyclodecylamido)zirconium diphenyl;
methylphenylsilyl(tetramethylcyclopentadienyl)-(cycloundecylamido)zirconium diphenyl;
methylphenylsilyl(tetramethylcyclopentadienyl)-(cyclododecylamido)zirconium diphenyl;
methylphenylsilyl(tetramethylcyclopentadienyl)-(sec-butylamido)zirconium diphenyl;
methylphenylsilyl(tetramethylcyclopentadienyl)-(n-octylamido)zirconium diphenyl;
methylphenylsilyl(tetramethylcyclopentadienyl)-(n-decylamido)zirconium diphenyl;
methylphenylsilyl(tetramethylcyclopentadienyl)-(n-octadecylamido)zirconium diphenyl;
diphenylsilyl(tetramethylcyclopentadienyl)-(cyclopropylamido)zirconium diphenyl;
diphenylsilyl(tetramethylcyclopentadienyl)-(cyclobutylamido)zirconium diphenyl;

diphenylsilyl(tetramethylcyclopentadienyl)-(cyclopentylamido)zirconium diphenyl;
diphenylsilyl(tetramethylcyclopentadienyl)-(cyclohexylamido)zirconium diphenyl;
diphenylsilyl(tetramethylcyclopentadienyl)-(cycloheptylamido)zirconium diphenyl;
diphenylsilyl(tetramethylcyclopentadienyl)-(cyclooctylamido)zirconium diphenyl;
diphenylsilyl(tetramethylcyclopentadienyl)-(cyclononylamido)zirconium diphenyl;
diphenylsilyl(tetramethylcyclopentadienyl)-(cyclodecylamido)zirconium diphenyl;
diphenylsilyl(tetramethylcyclopentadienyl)-(cycloundecylamido)zirconium diphenyl;
diphenylsilyl(tetramethylcyclopentadienyl)-(cyclododecylamido) zirconium diphenyl;
diphenylsilyl(tetramethylcyclopentadienyl)-(sec-butylamido)zirconium diphenyl;
diphenylsilyl(tetramethylcyclopentadienyl)-(n-octylamido) zirconium diphenyl;
diphenylsilyl(tetramethylcyclopentadienyl)-(n-decylamido)zirconium diphenyl;
diphenylsilyl(tetramethylcyclopentadienyl)-(n-octadecylamido)zirconium diphenyl;

The above specific examples wherein each Q is methyl or each Q is phenyl is prepared from the corresponding compound wherein each Q is chloro. The dichloro (both Q are Cl) species of each of the above compounds are also within Formula II.

Another preferred class of compounds of the present invention are those compounds represented by the formula:

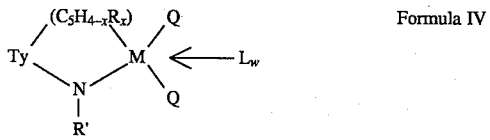

Formula IV wherein R, R', Q, M and $L_w$ are as defined above; wherein T is selected from radicals of the formula $(CR^3R^4)$ wherein $R^3$ and $R^4$ are independently selected from hydrogen and $C_1$–$C_{20}$ hydrocarbyl radicals; and wherein y is 1 or 2.

A more preferred class of compounds are those compounds represented by the above Formula IV wherein M is Ti. A most preferred class of compounds are those represented by the above Formula IV wherein M is Ti and wherein $R^3$ and $R^4$ are independently selected from hydrogen, $C_1$–$C_6$ alkyl radicals and $C_6$–$C_{12}$ aryl radicals.

Examples of specific compounds within the class of compounds defined by Formula IV include:

methylene(tetramethylcyclopentadienyl)-(cyclopropylamido)titanium dimethyl;
methylene(tetramethylcyclopentadienyl)-(cyclobutylamido)titanium dimethyl;
methylene(tetramethylcyclopentadienyl)-(cyclopentylamido)titanium dimethyl;
methylene(tetramethylcyclopentadienyl)-(cyclohexylamido)titanium dimethyl;
methylene(tetramethylcyclopentadienyl)-(cycloheptylamido)titanium dimethyl;
methylene(tetramethylcyclopentadienyl)-(cyclooctylamido)titanium dimethyl;
methylene(tetramethylcyclopentadienyl)-(cyclononylamido)titanium dimethyl;
methylene(tetramethylcyclopentadienyl)-(cyclodecylamido)titanium dimethyl;
methylene(tetramethylcyclopentadienyl)-(cycloundecylamido)titanium dimethyl;
methylene(tetramethylcyclopentadienyl)-(cyclododecylamido)titanium dimethyl;
methylene(tetramethylcyclopentadienyl)-(sec-butylamido)titanium dimethyl;
methylene(tetramethylcyclopentadienyl)-(n-octylamido)titanium dimethyl;
methylene(tetramethylcyclopentadienyl)-(n-decylamido)titanium dimethyl;
methylene(tetramethylcyclopentadienyl)-(n-octadecylamido)titanium dimethyl;
dimethylmethylene(tetramethylcyclopentadienyl)-(cyclopropylamido)titanium dimethyl;
dimethylmethylene(tetramethylcyclopentadienyl)-(cyclobutylamido)titanium dimethyl;
dimethylmethylene(tetramethylcyclopentadienyl)-(cyclopentylamido)titanium dimethyl;
dimethylmethylene(tetramethylcyclopentadienyl)-(cyclohexylamido)titanium dimethyl;
dimethylmethylene(tetramethylcyclopentadienyl)-(cycloheptylamido)titanium dimethyl;
dimethylmethylene(tetramethylcyclopentadienyl)-(cyclooctylamido)titanium dimethyl;
dimethylmethylene(tetramethylcyclopentadienyl)-(cyclononylamido)titanium dimethyl;
dimethylmethylene(tetramethylcyclopentadienyl)-(cyclodecylamido)titanium dimethyl;
dimethylmethylene(tetramethylcyclopentadienyl)-(cycloundecylamido)titanium dimethyl;
dimethylmethylene(tetramethylcyclopentadienyl)-(cyclododecylamido)titanium dimethyl;
dimethylmethylene(tetramethylcyclopentadienyl)-(sec-butylamido)titanium dimethyl;
dimethylmethylene(tetramethylcyclopentadienyl)-(n-octylamido)titanium dimethyl;
dimethylmethylene(tetramethylcyclopentadienyl)-(n-decylamido)titanium dimethyl;
dimethylmethylene(tetramethylcyclopentadienyl)-(n-octadecylamido)titanium dimethyl;
diethylmethylene(tetramethylcyclopentadienyl)-(cyclopropylamido)titanium dimethyl;
diethylmethylene(tetramethylcyclopentadienyl)-(cyclobutylamido)titanium dimethyl;
diethylmethylene(tetramethylcyclopentadienyl)-(cyclopentylamido)titanium dimethyl;
diethylmethylene(tetramethylcyclopentadienyl)-(cyclohexylamido)titanium dimethyl;
diethylmethylene(tetramethylcyclopentadienyl)-(cycloheptylamido)titanium dimethyl;
diethylmethylene(tetramethylcyclopentadienyl)-(cyclooctylamido)titanium dimethyl;
diethylmethylene(tetramethylcyclopentadienyl)-(cyclononylamido)titanium dimethyl;
diethylmethylene(tetramethylcyclopentadienyl)-(cyclodecylamido)titanium dimethyl;
diethylmethylene(tetramethylcyclopentadienyl)-(cycloundecylamido)titanium dimethyl;
diethylmethylene(tetramethylcyclopentadienyl)-(cyclododecylamido)titanium dimethyl;
diethylmethylene(tetramethylcyclopentadienyl)-(sec-butylamido)titanium dimethyl;

diethylmethylene(tetramethylcyclopentadienyl)-(n-octylamido)titanium dimethyl;
diethylmethylene(tetramethylcyclopentadienyl)-(n-decylamido)titanium dimethyl;
diethylmethylene(tetramethylcyclopentadienyl)-(n-octadecylamido)titanium dimethyl;
ethylene(tetramethylcyclopentadienyl)-(cyclopropylamido)titanium dimethyl;
ethylene(tetramethylcyclopentadienyl)-(cyclobutylamido)titanium dimethyl;
ethylene(tetramethylcyclopentadienyl)-(cyclopentylamido)titanium dimethyl;
ethylene(tetramethylcyclopentadienyl)-(cyclohexylamido)titanium dimethyl;
ethylene(tetramethylcyclopentadienyl)-(cycloheptylamido)titanium dimethyl;
ethylene(tetramethylcyclopentadienyl)-(cyclooctylamido)titanium dimethyl;
ethylene(tetramethylcyclopentadienyl)-(cyclononylamido)titanium dimethyl;
ethylene(tetramethylcyclopentadienyl)-(cyclodecylamido)titanium dimethyl;
ethylene(tetramethylcyclopentadienyl)-(cycloundecylamido)titanium dimethyl;
ethylene(tetramethylcyclopentadienyl)-(cyclododecylamido)titanium dimethyl;
ethylene(tetramethylcyclopentadienyl)-(sec-butylamido)titanium dimethyl;
ethylene(tetramethylcyclopentadienyl)-(n-octylamido)titanium dimethyl;
ethylene(tetramethylcyclopentadienyl)-(n-decylamido)titanium dimethyl;
ethylene(tetramethylcyclopentadienyl)-(n-octadecylamido)titanium dimethyl;
1,1-dimethylethylene(tetramethylcyclopentadienyl)-(cyclopropylamido)titanium dimethyl;
1,1-dimethylethylene(tetramethylcyclopentadienyl)-(cyclobutylamido)titanium dimethyl;
1,1-dimethylethylenetetramethylcyclopentadienyl)-(cyclopentylamido)titanium dimethyl;
1,1-dimethylethylenetetramethylcyclopentadienyl)-(cyclohexylamido)titanium dimethyl;
1,1-dimethylethylenetetramethylcyclopentadienyl)-(cycloheptylamido)titanium dimethyl;
1,1-dimethylethylenetetramethylcyclopentadienyl)-(cyclooctylamido)titanium dimethyl;
1,1-dimethylethylenetetramethylcyclopentadienyl)-(cyclononylamido)titanium dimethyl;
1,1-dimethylethylenetetramethylcyclopentadienyl)-(cyclodecylamido)titanium dimethyl;
1,1-dimethylethylenetetramethylcyclopentadienyl)-(cycloundecylamido)titanium dimethyl;
1,1-dimethylethylenetetramethylcyclopentadienyl)-(cyclododecylamido)titanium dimethyl;
1,1-dimethylethylenetetramethylcyclopentadienyl)-(sec-butylamido)titanium dimethyl;
1,1-dimethylethylenetetramethylcyclopentadienyl)-(n-octylamido)titanium dimethyl;
1,1-dimethylethylenetetramethylcyclopentadienyl)-(n-decylamido)titanium dimethyl;
1,1-dimethylethylenetetramethylcyclopentadienyl)-(n-octadecylamido)titanium dimethyl;
1,1-dipropylethylene(tetramethylcyclopentadienyl)-(cyclopropylamido)titanium dimethyl;
1,1-dipropylethylene(tetramethylcyclopentadienyl)-(cyclobutylamido)titanium dimethyl;
1,1-dipropylethylene(tetramethylcyclopentadienyl)-(cyclopentylamido)titanium dimethyl;
1,1-dipropylethylene(tetramethylcyclopentadienyl)-(cyclohexylamido)titanium dimethyl;
1,1-dipropylethylene(tetramethylcyclopentadienyl)-(cycloheptylamido)titanium dimethyl;
1,1-dipropylethylene(tetramethylcyclopentadienyl)-(cyclooctylamido)titanium dimethyl;
1,1-dipropylethylene(tetramethylcyclopentadienyl)-(cyclononylamido)titanium dimethyl;
1,1-dipropylethylene(tetramethylcyclopentadienyl)-(cyclodecylamido)titanium dimethyl;
1,1-dipropylethylene(tetramethylcyclopentadienyl)-(cycloundecylamido)titanium dimethyl;
1,1-dipropylethylene(tetramethylcyclopentadienyl)-(cyclododecylamido)titanium dimethyl;
1,1-dipropylethylene(tetramethylcyclopentadienyl)-(sec-butylamido)titanium dimethyl;
1,1-dipropylethylene(tetramethylcyclopentadienyl)-(n-octylamido)titanium dimethyl;
1,1-dipropylethylene(tetramethylcyclopentadienyl)-(n-decylamido)titanium dimethyl;
1,1-dipropylethylene(tetramethylcyclopentadienyl)-(n-octadecylamido)titanium dimethyl;
1,2-dimethylethylene(tetramethylcyclopentadienyl)-(cyclopropylamido)titanium dimethyl;
1,2-dimethylethylene(tetramethylcyclopentadienyl)-(cyclobutylamido)titanium dimethyl;
1,2-dimethylethylenetetramethylcyclopentadienyl)-(cyclopentylamido)titanium dimethyl;
1,2-dimethylethylenetetramethylcyclopentadienyl)-(cyclohexylamido)titanium dimethyl;
1,2-dimethylethylenetetramethylcyclopentadienyl)-(cycloheptylamido)titanium dimethyl;
1,2-dimethylethylenetetramethylcyclopentadienyl)-(cyclooctylamido)titanium dimethyl;
1,2-dimethylethylenetetramethylcyclopentadienyl)-(cyclononylamido)titanium dimethyl;
1,2-dimethylethylenetetramethylcyclopentadienyl)-(cyclodecylamido)titanium dimethyl;
1,2-dimethylethylenetetramethylcyclopentadienyl)-(cycloundecylamido)titanium dimethyl;
1,2-dimethylethylenetetramethylcyclopentadienyl)-(cyclododecylamido)titanium dimethyl;
1,2-dimethylethylenetetramethylcyclopentadienyl)-(sec-butylamido)titanium dimethyl;
1,2-dimethylethylenetetramethylcyclopentadienyl)-(n-octylamido)titanium dimethyl;
1,2-dimethylethylenetetramethylcyclopentadienyl)-(n-decylamido)titanium dimethyl;
1,2-dimethylethylenetetramethylcyclopentadienyl)-(n-octadecylamido)titanium dimethyl;
1,2-dipropylethylene(tetramethylcyclopentadienyl)-(cyclopropylamido)titanium dimethyl;
1,2-dipropylethylene(tetramethylcyclopentadienyl)-(cyclobutylamido)titanium dimethyl;
1,2-dipropylethylene(tetramethylcyclopentadienyl)-(cyclopentylamido)titanium dimethyl;

1,2-dipropylethylene(tetramethylcyclopentadienyl)-(cyclohexylamido)titanium dimethyl;
1,2-dipropylethylene(tetramethylcyclopentadienyl)-(cycloheptylamido)titanium dimethyl;
1,2-dipropylethylene(tetramethylcyclopentadienyl)-(cyclooctylamido)titanium dimethyl;
1,2-dipropylethylene(tetramethylcyclopentadienyl)-(cyclononylamido)titanium dimethyl;
1,2-dipropylethylene(tetramethylcyclopentadienyl)-(cyclodecylamido)titanium dimethyl;
1,2-dipropylethylene(tetramethylcyclopentadienyl)-(cycloundecylamido)titanium dimethyl;
1,2-dipropylethylene(tetramethylcyclopentadienyl)-(cyclododecylamido)titanium dimethyl;
1,2-dipropylethylene(tetramethylcyclopentadienyl)-(sec-butylamido)titanium dimethyl;
1,2-dipropylethylene(tetramethylcyclopentadienyl)-(n-octylamido)titanium dimethyl;
1,2-dipropylethylene(tetramethylcyclopentadienyl)-(n-decylamido)titanium dimethyl;
1,2-dipropylethylene(tetramethylcyclopentadienyl)-(n-octadecylamido)titanium dimethyl;
2,2-dimethylethylene(tetramethylcyclopentadienyl)-(cyclopropylamido)titanium dimethyl;
2,2-dimethylethylene(tetramethylcyclopentadienyl)-(cyclobutylamido)titanium dimethyl;
2,2-dimethylethylenetetramethylcyclopentadienyl)-(cyclopentylamido)titanium dimethyl;
2,2-dimethylethylenetetramethylcyclopentadienyl)-(cyclohexylamido)titanium dimethyl;
2,2-dimethylethylenetetramethylcyclopentadienyl)-(cycloheptylamido)titanium dimethyl;
2,2-dimethylethylenetetramethylcyclopentadienyl)-(cyclooctylamido)titanium dimethyl;
2,2-dimethylethylenetetramethylcyclopentadienyl)-(cyclononylamido)titanium dimethyl;
2,2-dimethylethylenetetramethylcyclopentadienyl)-(cyclodecylamido)titanium dimethyl;
2,2-dimethylethylenetetramethylcyclopentadienyl)-(cycloundecylamido)titanium dimethyl;
2,2-dimethylethylenetetramethylcyclopentadienyl)-(cyclododecylamido)titanium dimethyl;
2,2-dimethylethylenetetramethylcyclopentadienyl)-(sec-butylamido)titanium dimethyl;
2,2-dimethylethylenetetramethylcyclopentadienyl)-(n-octylamido)titanium dimethyl;
2,2-dimethylethylenetetramethylcyclopentadienyl)-(n-decylamido)titanium dimethyl;
2,2-dimethylethylenetetramethylcyclopentadienyl)-(n-octadecylamido)titanium dimethyl;
2,2-dipropylethylene(tetramethylcyclopentadienyl)-(cyclopropylamido)titanium dimethyl;
2,2-dipropylethylene(tetramethylcyclopentadienyl)-(cyclobutylamido)titanium dimethyl;
2,2-dipropylethylene(tetramethylcyclopentadienyl)-(cyclopentylamido)titanium dimethyl;
2,2-dipropylethylene(tetramethylcyclopentadienyl)-(cyclohexylamido)titanium dimethyl;
2,2-dipropylethylene(tetramethylcyclopentadienyl)-(cycloheptylamido)titanium dimethyl;
2,2-dipropylethylene(tetramethylcyclopentadienyl)-(cyclooctylamido)titanium dimethyl;
2,2-dipropylethylene(tetramethylcyclopentadienyl)-(cyclononylamido)titanium dimethyl;
2,2-dipropylethylene(tetramethylcyclopentadienyl)-(cyclodecylamido)titanium dimethyl;
2,2-dipropylethylene(tetramethylcyclopentadienyl)-(cycloundecylamido)titanium dimethyl;
2,2-dipropylethylene(tetramethylcyclopentadienyl)-(cyclododecylamido)titanium dimethyl;
2,2-dipropylethylene(tetramethylcyclopentadienyl)-(sec-butylamido)titanium dimethyl;
2,2-dipropylethylene(tetramethylcyclopentadienyl)-(n-octylamido)titanium dimethyl;
2,2-dipropylethylene(tetramethylcyclopentadienyl)-(n-decylamido)titanium dimethyl;
2,2-dipropylethylene(tetramethylcyclopentadienyl)-(n-octadecylamido)titanium dimethyl;
1,1-diphenylethylene(tetramethylcyclopentadienyl)-(cyclopropylamido)titanium dimethyl;
1,1-diphenylethylene(tetramethylcyclopentadienyl)-(cyclobutylamido)titanium dimethyl;
1,1-diphenylethylene(tetramethylcyclopentadienyl)-(cyclopentylamido)titanium dimethyl;
1,1-diphenylethylene(tetramethylcyclopentadienyl)-(cyclohexylamido)titanium dimethyl;
1,1-diphenylethylene(tetramethylcyclopentadienyl)-(cycloheptylamido)titanium dimethyl;
1,1-diphenylethylene(tetramethylcyclopentadienyl)-(cyclooctylamido)titanium dimethyl;
1,1-diphenylethylene(tetramethylcyclopentadienyl)-(cyclononylamido)titanium dimethyl;
1,1-diphenylethylene(tetramethylcyclopentadienyl)-(cyclodecylamido)titanium dimethyl;
1,1-diphenylethylene(tetramethylcyclopentadienyl)-(cycloundecylamido)titanium dimethyl;
1,1-diphenylethylene(tetramethylcyclopentadienyl)-(cyclododecylamido)titanium dimethyl;
1,1-diphenylethylene(tetramethylcyclopentadienyl)-(sec-butylamido)titanium dimethyl;
1,1-diphenylethylene(tetramethylcyclopentadienyl)-(n-octylamido)titanium dimethyl;
1,1-diphenylethylene(tetramethylcyclopentadienyl)-(n-decylamido)titanium dimethyl;
1,1-diphenylethylene(tetramethylcyclopentadienyl)-(n-octadecylamido)titanium dimethyl;
1,2-diphenylethylene(tetramethylcyclopentadienyl)-(cyclopropylamido)titanium dimethyl;
1,2-diphenylethylene(tetramethylcyclopentadienyl)-(cyclobutylamido)titanium dimethyl;
1,2-diphenylethylene(tetramethylcyclopentadienyl)-(cyclopentylamido)titanium dimethyl;
1,2-diphenylethylene(tetramethylcyclopentadienyl)-(cyclohexylamido)titanium dimethyl;
1,2-diphenylethylene(tetramethylcyclopentadienyl)-(cycloheptylamido)titanium dimethyl;
1,2-diphenylethylene(tetramethylcyclopentadienyl)-(cyclooctylamido)titanium dimethyl;
1,2-diphenylethylene(tetramethylcyclopentadienyl)-(cyclononylamido)titanium dimethyl;
1,2-diphenylethylene(tetramethylcyclopentadienyl)-(cyclodecylamido)titanium dimethyl;
1,2-diphenylethylene(tetramethylcyclopentadienyl)-(cycloundecylamido)titanium dimethyl;

1,2-diphenylethylene(tetramethylcyclopentadienyl)-(cyclododecylamido)titanium dimethyl;

1,2-diphenylethylene(tetramethylcyclopentadienyl)-(sec-butylamido)titanium dimethyl;

1,2-diphenylethylene(tetramethylcyclopentadienyl)-(n-octylamido)titanium dimethyl;

1,2-diphenylethylene(tetramethylcyclopentadienyl)-(n-decylamido)titanium dimethyl;

1,2-diphenylethylene(tetramethylcyclopentadienyl)-(n-octadecylamido)titanium dimethyl;

2,2-diphenylethylene(tetramethylcyclopentadienyl)-(cyclopropylamido)titanium dimethyl;

2,2-diphenylethylene(tetramethylcyclopentadienyl)-(cyclobutylamido)titanium dimethyl;

2,2-diphenylethylene(tetramethylcyclopentadienyl)-(cyclopentylamido)titanium dimethyl;

2,2-diphenylethylene(tetramethylcyclopentadienyl)-(cyclohexylamido)titanium dimethyl;

2,2-diphenylethylene(tetramethylcyclopentadienyl)-(cycloheptylamido)titanium dimethyl;

2,2-diphenylethylene(tetramethylcyclopentadienyl)-(cyclooctylamido)titanium dimethyl;

2,2-diphenylethylene(tetramethylcyclopentadienyl)-(cyclononylamido)titanium dimethyl;

2,2-diphenylethylene(tetramethylcyclopentadienyl)-(cyclodecylamido)titanium dimethyl;

2,2-diphenylethylene(tetramethylcyclopentadienyl)-(cycloundecylamido)titanium dimethyl;

2,2-diphenylethylene(tetramethylcyclopentadienyl)-(cyclododecylamido)titanium dimethyl;

2,2-diphenylethylene(tetramethylcyclopentadienyl)-(sec-butylamido)titanium dimethyl;

2,2-diphenylethylene(tetramethylcyclopentadienyl)-(n-octylamido)titanium dimethyl;

2,2-diphenylethylene(tetramethylcyclopentadienyl)-(n-decylamido)titanium dimethyl;

2,2-diphenylethylene(tetramethylcyclopentadienyl)-(n-octadecylamido)titanium dimethyl;

The above named specific compounds wherein each Q is methyl are prepared from the corresponding compound wherein each Q is chloro. Thus, specific compounds within Formula IV are those wherein each Q is chloro. Also, the corresponding compounds wherein each Q is phenyl, M is zirconium or hafnium in place of titanium and $(CR^3R^4)y$ is methylphenylmethylene, tetramethylethylene or tetraethylethylene are also specific compounds within the above Formula IV.

Herein a 1° carbon atom is one which is a methyl radical or a carbon atom which is bonded to only one other carbon atom; a 2° carbon atom is one which is bonded to only two other carbon atoms, and a 3° carbon atom is bonded to three other carbon atoms. Preferably the R' alicyclic or aliphatic hydrocarbyl group has three or more carbon atoms and is bonded to the nitrogen atom through a 2° carbon atom; most preferably the hydrocarbyl group is alicyclic.

Mono(cyclopentadienyl) metal compounds of the present invention have been discovered to produce a highly productive catalyst system which produces an ethylene-α-olefin copolymer of significantly greater molecular weight and α-olefin comonomer content as compared with other species of mono(cyclopentadienyl) metal compounds when utilized in an otherwise identical catalyst system under identical polymerization conditions. Further, within this subgenus of metal compounds it has been found that the nature and degree of substitution groups (R) of the cyclopentadienyl ring can be varied to produce a catalyst system having a "catalyst reactivity ratio $(r_1)$" which may be varied from a high to a low value as may be most desired to best suit the catalyst system to a particular type of polymerization process. Particularly it has been found that as the number of substituents (R), which are preferably hydrocarbyl substituents increases, the reactivity ratio $(r_1)$ decreases, the lowest reactivity ratios being obtained by a titanium compound having a tetrahydrocarbyl substituted cyclopentadienyl group, preferably a tetramethylcyclopentadienyl group.

The most preferred class of cyclopentadienyl metal compounds are represented by the formula:

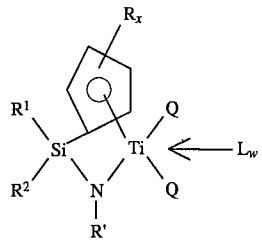

Formula V wherein Q, L, R', R, "x" and "w" are as previously defined and $R^1$ and $R^2$ are each independently selected from $C_1$ to $C_{20}$ hydrocarbyl radicals wherein one or more hydrogen atoms is replaced by a halogen atom; $R^1$ and $R^2$ may also be joined forming a $C_3$ to $C_{20}$ ring which incorporates the silicon bridge.

Among this class of compounds of Formula V, various substituent and ligand affects have been discovered which significantly affect the properties of a catalyst system. The nature and degree of substitutions (R) in the cyclopentadienyl ring was found to significantly influence the catalyst ability to incorporate α-olefin comonomers when producing an ethylene-α-olefin copolymer. For the greatest amount of comonomer incorporation, the cyclopentadienyl ring should be fully substituted (x=4) with hydrocarbyl groups (R), most preferably methyl groups. This affect is demonstrated by a comparison between Examples 83 to 85. Next, the nature of the R' ligand of the amido group significantly influences the capability of a catalyst to incorporate α-olefin comonomer. Amido group R' ligands which are aliphatic or alicyclic hydrocarbyl ligands bonded to the nitrogen atom through a 1° or 2° carbon atom provide for a greater degree of α-olefin comonomer incorporation than do R' groups bonded through a 3° carbon atom or bearing aromatic carbon atoms. Further, wherein the R' ligand is bonded to the nitrogen atom through a 2° carbon atom, the activity of the catalyst is greater when the R' substituent is alicyclic than when R' is bonded to the nitrogen through a 1° carbon atom of an aliphatic group of identical carbon number. With regard to an alicyclic hydrocarbyl R' ligand it has been found that as the number of carbon atoms thereof increases the molecular weight of the ethylene-α-olefin copolymer increases while the amount of α-olefin comonomer incorporated remains about the same or increases. Further, as the carbon number of the alicyclic hydrocarbyl ligand increases the productivity of the catalyst system increases. This is demonstrated by Examples 71–76. Accordingly, the R' ligand most preferred is cyclododecyl $(C_{12}H_{23})$.

The effect of the bridging group ligands $R^1$ and $R^2$ has been found to be of less significance. The nature of the $R^1$ and $R^2$ ligands exerts a small effect upon the activity of a catalyst. For greatest catalyst activity the $R^1$ and $R^2$ ligands are preferably alkyl, most preferably methyl. The Q anionic ligands of the transition metal have not been observed to exert any particular influence on the catalyst or polymer properties, as demonstrated by comparison of Examples 71 and 86. Accordingly, as a convenience in the production of the transitional metal component the Q ligands are preferably chlorine or methyl.

The compounds most preferred for reasons of their high catalyst activity in combination with an ability to produce high molecular weight ethylene-α-olefin copolymers of high comonomer content is represented by the formula

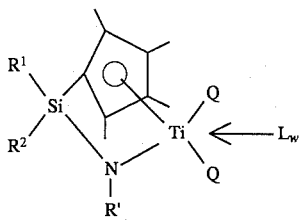

Formula VI wherein $R^1$ and $R^2$ are each independently a $C_1$ to $C_3$ hydrocarbyl radical, each Q is independently a halide or alkyl radical, R' is an aliphatic or an alicyclic hydrocarby radical of the formula $(C_nH_{2n+b})$ wherein "n" is a number from 3 to 20 and "b" is +1 in which case the ligand is aliphatic or −1 in which case the ligand is alicyclic. Of these compounds, the most preferred is that compound wherein $R^1$ and $R^2$ are methyl, each Q is methyl, n is 12, and the hydrocarbyl radical is alicyclic (i.e., b is −1). Most preferred is that compound wherein the $(C_nH2n-1)$ hydrocarbyl radical is a cyclododecyl group. Hereafter this compound is referred to for convenience as $Me_2Si(C_5Me_4)(NC_{12}H_{23})TiQ_2$.

All of the above-defined mono(cyclopentadienyl) metal compounds are useful, in combination with an activator or cocatalyst, to polymerize α-olefins. Suitable activators include alumoxanes and activators comprising a cation and a non-coordinating compatible anion.

The alumoxane component is an oligomeric compound which may be represented by the general formula $(R^3—Al—O)_m$ which is a cyclic compound, or may be $R^4(R^5—Al—O—)_m—AlR^6_2$ which is a linear compound. An alumoxane is generally a mixture of both the linear and cyclic compounds. In the general alumoxane formula $R^3$, $R^4$, $R^5$ and $R^6$ are, independently a $C_{1-5}$ alkyl radical, for example, methyl, ethyl, propyl, butyl or pentyl and "m" is an integer from 1 to about 50. Most preferably, $R^3$, $R^4$, $R^5$ and $R^6$ are each methyl and "m" is at least 4. When an alkyl aluminum halide is employed in the preparation of the alumoxane, one or more $R^{3-6}$ groups may be halide.

As is now well known, alumoxanes can be prepared by various procedures. For example, a trialkyl aluminum may be reacted with water, in the form of a moist inert organic solvent; or the trialkyl aluminum may be contacted with a hydrated salt, such as hydrated copper sulfate suspended in an inert organic solvent, to yield an alumoxane. Generally, however prepared, the reaction of a trialkyl aluminum with a limited amount of water yields a mixture of both linear and cyclic species of alumoxane.

Suitable alumoxanes utilized in the catalyst systems of this invention are those prepared by the hydrolysis of a trialkylaluminum; such as trimethylaluminum, triethylaluminum, tripropylaluminum; triisobutylaluminum, dimethylaluminumchloride, diisobutylaluminumchloride, diethylaluminumchloride, and the like. The most preferred alumoxane for use is methylalumoxane (MAO). Methylalumoxanes having an average degree of oligomerization of from about 4 to about 25 ("m"=4 to 25), with a range of 13 to 25, are the most preferred.

Activators comprising a non-coordinating compatible anion component are described in U.S. Pat. No. 5,198,401 which is incorporated herein by reference. Compounds useful as the activator compound, in the preparation of the catalyst comprise a cation, preferably a Bronsted acid capable of donating a proton, and a compatible non-coordinating anion containing a single coordination complex comprising a charge-bearing metal or metalloid core which is relatively large (bulky), capable of stabilizing the active catalyst species (the Group IV-B cation) which is formed when the metallocene and activator compounds are combined, and said anion is sufficiently labile to be displaced by olefinic, diolefinic and acetylenically unsaturated substrates or other neutral Lewis bases such as ethers, nitriles and the like. It is well known that reactive cations other than Bronsted acids capable of donating a proton are also useful. Examples of such other cations include ferrocenium triphenylcarbonium and triethylsilylinium cations. Any metal or metalloid capable of forming a coordination complex which is resistant to degradation by water (or other Bronsted or Lewis Acids) may be used or contained in the anion of the second activator compound. Suitable metals include, but are not limited to, aluminum, gold, platinum and the like. Suitable metalloids include, but are not limited to, boron, phosphorus, silicon and the like.

Compounds containing anions which comprise coordination complexes containing a single metal or metalloid atom are, of course, well known and many, particularly compounds containing a single boron atom in the anion portion, are available commercially. In light of this, salts containing anions comprising a coordination complex containing a single boron atom are preferred. In general, the second activator compounds useful in the preparation of the catalysts of this invention may be represented by the following general formula:

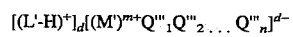

wherein:

L' is a neutral Lewis base;

H is a hydrogen atom;

[L'-H] is a Bronsted acid;

M' is a metal or metalloid;

$Q'''_1$ to $Q'''_n$ are, independently, hydride radicals, bridged or unbridged dialkylamido radicals, alkoxide and aryloxide radicals, hydrocarbyl and substituted hydrocarbyl radicals, halocarbyl and substituted halocarbyl radicals, and hydrocarbyl- and halocarbyl-substituted organometalloid radicals and any one, but not more than one, of $Q_1$ to $Q_n$ may be a halide radical;

m is an integer representing the formal valence charge of M';

n is the total number of ligands Q; and d is an integer representing the total charge on the anion.

Activator compounds comprising boron which are particularly useful in the preparation of catalysts of this invention are represented by the following general formula:

wherein:

L' is a neutral Lewis base;

H is a hydrogen atom;

[L'-H]⁺ is a Bronsted acid;

B is boron in a valence state of 3⁺;

$Ar_1$ and $Ar_2$ are the same or different substituted-aromatic hydrocarbon radicals and may be linked to each other through a stable bridging group; and $X_3$ and $X_4$ are, independently, hydride radicals, halide radicals, with the proviso that only $X_3$ or $X_4$ will be halide, hydrocarbyl radicals, substituted-hydrocarbyl radicals, halocarbyl radicals, substituted-halocarbyl radicals, hydrocarbyl- and halocarbyl-substituted organometalloid radicals, dialkylamido radicals, and alkoxy and aryloxy radicals.

In general, $Ar_1$ and $Ar_2$ may, independently, be any aromatic or substituted-aromatic hydrocarbon radical. Suitable aromatic radicals include, but are not limited to, phenyl, naphthyl and anthracenyl radicals. Suitable substituents on useful substituted-aromatic hydrocarbon radicals, include, but are not necessarily limited to, hydrocarbyl radicals, organometalloid radicals, alkoxy radicals, alkylamido radicals, fluoro and fluorohydrocarbyl radicals and the like such as those useful as $X_3$ or $X_4$. The substituent may be ortho, meta or para, relative to the carbon atom bonded to the boron atom. When either or both $X_3$ and $X_4$ are a hydrocarbyl radical, each may be the same or a different aromatic or substituted-aromatic radical as are $Ar_1$ and $Ar_2$, or the same may be a straight or branched alkyl, alkenyl or alkynyl radical, a cyclic hydrocarbon radical or an alkylsubstituted cyclic hydrocarbon radical. $X_3$ and $X_4$ may also, independently, be alkoxy or dialkylamido radicals, hydrocarbyl radicals and organometalloid radicals and the like. As indicated supra, $Ar_1$ and $Ar_2$ may be linked to each other. Similarly, either or both of $Ar_1$ and $Ar_2$ could be linked to either $X_3$ or $X_4$. Finally, $X_3$ and $X_4$ may also be linked to each other through a suitable bridging group.

Illustrative, but not limiting, examples of boron compounds which may be used as an activator component in the preparation of the improved catalysts of this invention are trialkyl-substituted ammonium salts such as triethylammonium tetra(phenyl)boron, tripropylammonium tetra(phenyl)boron, tri(n-butyl)ammonium tetra(phenyl)boron, trimethylammonium tetra(p-tolyl)boron, trimethylammonium tetra(o-tolyl)boron, tributylammonium tetra(pentafluorophenyl)boron, tripropylammonium tetra(o,p-dimethylphenyl)boron, tributylammonium tetra(m,m-dimethylphenyl) boron, tributylammonium tetra(p-trifluoromethylphenyl)boron, tributylammonium tetra(pentafluorophenyl)boron, tri(n-butyl)ammonium tetra(o-tolyl)boron and the like; N,N-dialkyl anilinium salts such as N,N-dimethylanilinium tetra(phenyl)boron, N,N-diethylanilinium tetra(phenyl)boron, N,N-2,4,6-pentamethylanilinium tetra(phenyl)boron and the like; dialkyl ammonium salts such as di (isopropyl)ammonium tetra(pentafluorophenyl)boron, dicyclohexylammonium tetra(phenyl)boron, and the like; and triaryl phosphonium salts such as triphenylphosphonium tetra(phenyl)boron, tri(methylphenyl)phosphonium tetra(phenyl)boron, tri(dimethylphenyl)phosphonium tetra(phenyl)boron and the like.

Similar lists of suitable compounds containing other metals and metalloids which are useful as activator components could be made, but such lists are not deemed necessary to a complete disclosure. In this regard, it should be noted that the foregoing list is not intended to be exhaustive and other boron compounds that would be useful as well as useful compounds containing other metals or metalloids would be readily apparent, from the foregoing general equations, to those skilled in the art.

It is important to continued polymerization operations that either the metal cation initially formed from the metallocene, or a decomposition product thereof, be a relatively stable catalyst. It is also important that the anion of the activator compound be chemically stable and bulky. Further, when the cation of the activator component is a Bronsted acid, it is important that the acidity of the activator compound be sufficient, relative to the metallocene, to facilitate the needed proton transfer. Conversely, the basicity of the metal complex must also be sufficient to facilitate the needed proton transfer. In general, metallocenes in which the Q ligands can be hydrolyzed by aqueous solutions can be considered suitable metallocenes for forming the catalysts described herein, because water (our reference Bronsted acid) is a weaker acid than the ammonium ions used as cation in our preferred ion-exchange reagents. This concept allows one of ordinary skill in the art to choose useful metallocene components because stability to water is a basic chemical property easily determined experimentally or by using the chemical literature.

In view of the above, when utilizing an activator comprising a non-coordinating compatible anion, the metal component should be one wherein each Q is selected from the group consisting of hydride and substituted and unsubstituted hydrocarbyl radicals. Preferred Q ligands are hydride, $C_1$–$C_{12}$ alkyl and $C_6$–$C_{12}$ aryl radicals. Most preferred are those Q ligands selected from methyl and phenyl radicals, particularly methyl radicals. The preferred metal components species for use with an activator comprising a non-coordinating compatible anion are those set forth above wherein each Q is methyl or phenyl.

The chemical reactions which occur upon combination of a monocyclopentadienyl metal compound with a non-coordinating compatible anion activator compound may be represented by reference to the general formulae set forth herein as follows:

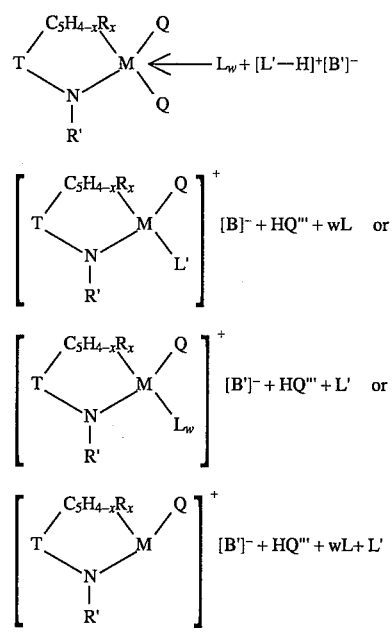

B' represents a compatible ion corresponding to the general formulae set forth above. When the mono(cyclopentadienyl) metal compound and the non-coordinating compatible anion activator components used to prepare the improved catalysts of the present invention are combined in a suitable solvent or diluent, all or a part of the cation of the activator (the acidic proton) combines with one of the substituents on the metallocene compound. In the case where the metallocene component has a formula corresponding to that of the general formula above, a neutral compound is liberated, which neutral compound either remains in solution or is liberated as a gas. In this regard, it should be noted that if either Q in the metallocene component is a hydride, hydrogen gas may be liberated. Similarly, if either Q is a methyl radical, methane may be liberated as a gas. In the cases where the first component has a formula corresponding to those of general formulae of the reaction sequence shown directly above, one of the substituents on the is protonated but no substituent is liberated. In general, the rate of formation of the products in the foregoing reaction equations will vary depending upon the choice of the solvent, the acidity of the $[L'-H]^+$ selected, the particular L', the anion, the temperature at which the reaction is completed and the particular cyclopentadienyl derivative of the metal selected.

As indicated, the improved catalyst compositions of the present invention will, preferably, be prepared in a suitable solvent or diluent. Suitable solvents or diluents include any of the solvents known in the prior art to be useful as solvents in the polymerization of olefins, diolefins and acetylenically unsaturated monomers. Suitable solvents, then, include, but are not necessarily limited to, straight and branched-chain hydrocarbons such as isobutane, butane, pentane, hexane, heptane, octane and the like; cyclic and alicyclic hydrocarbons such as cyclohexane, cycloheptane, methylcyclohexane, methylcycloheptane and the like and aromatic and alkyl-substituted aromatic compounds such as benzene, toluene, xylene and the like. Suitable solvents also include liquid olefins which may act as monomers or comonomers including ethylene, propylene, butadiene, cyclopentene, 1-hexane, 3-methyl-l-pentene, 4-methyl-1-pentene, 1,4-hexadiene, 1-octene, 1-decene and the like. Suitable solvents further include basic solvents which are not generally useful as polymerization solvents when conventional Ziegler-Natta type polymerization catalysts are used such as chlorobenzene.

Catalysts of this invention which are highly productive may be prepared at ratios of mono(cyclopentadienyl) metal compound to non-coordinating compatible anion activator of 10:1 to about 1:1, preferably about 3:1 to 1:1.

With respect to the combination of a mono(cyclopentadienyl) metal compound and non-coordinating compatible anion activator compound to form a catalyst of this invention, it should be noted that the two compounds combined for preparation of the active catalyst must be selected so as to avoid transfer of a fragment of the activator compound anion, particularly an aryl group, to the mono(cyclopentadienyl) metal cation, thereby forming a catalytically inactive species. When anions consisting of hydrocarbyl anions are used, there are several means of preventing anion degradation and formation of inactive species. One method is to carry out the protonolysis process in the presence of small Lewis bases such as tetrahydrofuran. Discrete complexes can be isolated from these reactions, but the Lewis base is insufficiently labile to be displaced readily by olefin monomers, resulting in, at best, catalysts of very low activity. Another method of avoiding deleterious anion degradation is by steric hindrance. Anions of the second component which contain aryl groups can be made more resistant to degradation by introducing substituents in the ortho positions of the phenyl rings. While active metallocene polymerization catalysts can be generated by this method, the complex reaction chemistry often prevents characterization of the catalytically active species. Steric hindrance can also result from substitutions on the cyclopentadienyl rings of the mono(cyclopentadienyl) metal compound component. Hence, wherein the mono(cyclopentadienyl) metal compound used is a [peralkyl-substituted mono(cyclopentadienyl)] Group IVB metal compound, the high degree of substitution on the cyclopentadienyl ring creates sufficient bulkiness that the Lewis base generated by the protonolysis reaction not only cannot coordinate to the metal but also polyarylborate anions without substituents on the aryl rings do not transfer aryl fragments to generate catalytically inactive species.

Another means of rendering the anion of the activator compound more resistant to degradation is afforded by fluoride substitution, especially perfluoro substitution, in the anion thereof. One class of suitable non-coordinating anions can be represented by the formula $[B(C_6F_5)_3Q''']^-$ where $Q'''$ is a monoanionic non-bridging radical as described above. The preferred anion of the activator compound of this invention, tetra(pentafluorophenyl)boron, hereafter referred to for convenience by the notation $[B(C_6F_5)_4]^-$, or $[B(pfp)_4]^-$, is virtually impervious to degradation and can be used with a much wider range of mono(cyclopentadienyl) metal cations, including those without substitution on the cyclopentadienyl rings, than anions comprising hydrocarbyl radicals. The tetra(pentafluoro)boron anion is illustrated below:

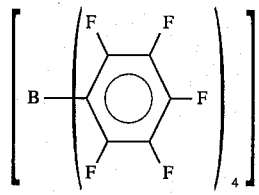

Since this anion has little or no ability to coordinate to the mono(cyclopentadienyl) metal cation and is not degraded by the mono(cyclopentadienyl) metal cation, structures of the ion-pair catalysts using the $[B(pfp)_4]^-$ anion depend on steric hindrance of substituents on the cyclopentadienyl rings of mono(cyclopentadienyl) metal compound the nature of the cation of the activator component, the Lewis base liberated from the protonolysis reaction, and the ratio at which the mono(cyclopentadienyl) metal and activator component are combined. Thus, preferred catalyst systems having a non-coordinating compatible ion activator are those compounds of the above Formulas I–V, and, specifically, those species set forth above, in combination with $[B(pfp)_4]^-$. If Lewis bases other than that liberated from the proton transfer process are present, they may complex to the metal to form modified catalysts of this invention.

Catalyst Systems

The catalyst systems employed in the method of the invention comprise a complex formed upon admixture of the metal component with an activator component. The catalyst system may be prepared by addition of the requisite metal component and either one or more alumoxane components or one or more non-coordinating anion components, or a combination of both, to an inert solvent in which olefin polymerization can be carried out by a solution, slurry or bulk phase polymerization procedure.

The catalyst system may be conveniently prepared by placing the selected metal component and the selected activator component, in any order of addition, in an alkane or aromatic hydrocarbon solvent—preferably one which is also suitable for service as a polymerization diluent. Where the hydrocarbon solvent utilized is also suitable for use as a polymerization diluent, the catalyst system may be prepared in situ in the polymerization reactor. Alternatively, the catalyst system may be separately prepared, in concentrated form, and added to the polymerization diluent in a reactor. Or, if desired, the components of the catalyst system may be prepared as separate solutions and added to the polymerization diluent in a reactor, in appropriate ratios, as is suitable for a continuous liquid phase polymerization reaction procedure. Alkane and aromatic hydrocarbons suitable as solvents for formation of the catalyst system and also as a polymerization diluent are exemplified by, but are not necessarily limited to, straight and branched chain hydrocarbons such as isobutane, butane, pentane, hexane, heptane, octane and the like, cyclic and alicyclic hydrocarbons such as cyclohexane, cycloheptane, methylcyclohexane, methylcycloheptane and the like, and aromatic and alkyl-substituted aromatic compounds such as benzene, toluene, xylene and the like. Suitable solvents also include liquid olefins which may act as monomers or comonomers including ethylene, propylene, 1-butene, 1-hexene and the like.

In accordance with this invention, when the activator is alumoxane, optimum results are generally obtained wherein the Group IV B metal compound is present in the polymerization diluent in a concentration of from about 0.0001 to about 1.0 millimoles/liter of diluent and the alumoxane component is present in an amount to provide a molar aluminum to transition metal ratio of from about 1:1 to about 20,000:1. Where the activator is one comprising a non-coordinating compatible anion and a cation, such activator is present in an amount sufficient to provide a molar ratio of metal component of from 10:1 to about 1:1. Sufficient solvent should be employed so as to provide adequate heat transfer away from the catalyst components during reaction and to permit good mixing.

The catalyst system ingredients—that is, the Group IV B metal component, the activator, and polymerization diluent—can be added to the reaction vessel rapidly or slowly. The temperature maintained during the contact of the catalyst components can vary widely, such as, for example, from −100° to 300° C. Greater or lesser temperatures can also be employed. Preferably, during formation of the catalyst system, the reaction is maintained within a temperature of from about 25° to 100° C., most preferably about 25°.

Polymerization process

A typical polymerization process of the invention comprises the steps of contacting ethylene and a $C_3$–$C_{20}$ α-olefin alone, or with other unsaturated monomers including $C_3$–$C_{20}$ α-olefins, $C_4$–$C_{20}$ diolefins, and/or acetylenically unsaturated monomers with a catalyst comprising, in a suitable polymerization diluent, a mono(cyclopentadienyl) metal compound, as described above, and an activator. For example, a catalyst comprising a mono(cyclopentadienyl) metal compound as described above and either 1) a non-coordinating compatible anion activator or 2) an alumoxane activator. The alumoxane activator is utilized in an amount to provide a molar aluminum to titanium metal ratio of from about 1:1 to about 20,000:1 or more. The non-coordinating compatible anion activator is utilized in an amount to provide a molar ratio of monocyclopentadienyl metal compound to non-coordinating anion of 10:1 to about 1:1. The above reaction is conducted by reacting such monomers in the presence of such catalyst system at a temperature of from about −100° C. to about 300° C. for a time of from about 1 second to about 10 hours to produce a copolymer having a weight average molecular weight of from about 1,000 or less to about 5,000,000 or more and a molecular weight distribution of from about 1.5 to about 15.0.

In a preferred embodiment of the process of this invention the catalyst system is utilized in the liquid phase (slurry, solution, suspension or bulk phase or combination thereof), high pressure fluid phase or gas phase polymerization of an olefin monomer. When utilized in a gas phase, slurry phase or suspension phase polymerization, the catalyst systems will preferably be supported catalyst systems. See, for example, U.S. Pat. No. 5,057,475 which is incorporated herein by reference. Such catalyst systems can also include other well known additives such as, for example, scavengers. See, for example, U.S. Pat. No. 5,153,157 which is incorporated herein by reference. These processes may be employed singularly or in series. The liquid phase process comprises the steps of contacting an ethylene and an α-olefin monomer with the catalyst system in a suitable polymerization diluent and reacting the monomers in the presence of the catalyst system for a time and at a temperature sufficient to produce an ethylene-α-olefin copolymer of high molecular weight.

The monomers for such process comprise ethylene in combination with an α-olefin having 3 to 20 carbon atoms, preferably 3 to 10 carbon atoms, most preferably 3 to 8 carbon atoms, for the production of an ethylene-α-olefin copolymer. It should be appreciated that the advantages as observed in an ethylene-α-olefin copolymer produced with a catalyst system of this invention would also be expected to be obtained in a copolymer of different α-olefins wherein ethylene is not used as a monomer as viewed in comparison to a copolymer of the same or different α-olefins produced under similar polymerization conditions with a catalyst system which does not use a monocyclopentadienyl Group IV B metal compound as defined herein. Accordingly, although this invention is described with reference to an ethylene-α-olefin copolymer and the advantages of the defined catalyst system for the production thereof, this invention is not to be understood to be limited to the production of an ethylene-α-olefin copolymer, but instead the catalyst system hereof is to be understood to be advantageous in the same respects to the production of a copolymer composed of two or more $C_3$ or higher α-olefin monomers. Copolymers of higher α-olefin such as propylene, butene, styrene or higher α-olefins and diolefins can also be prepared. Conditions most preferred for the homo- or copolymerization of ethylene are those wherein ethylene is submitted to the reaction zone at pressures of from about 0.019 psia to about 50,000 psia and the reaction temperature is maintained at from about −100° to about 300° C. Where the activator is an alumoxane, the aluminum to titanium metal molar ratio is preferably from about 1:1 to 20,000 to 1. A more preferable range would be 1:1 to 2000:1. The reaction time is preferably from about 10 seconds to about 1 hour.

The α-olefin to ethylene molar ratio often bears importantly upon the production capacity of a reactor of any design—i.e., whether for solution or gas phase production, etc.—for production of an ethylene based copolymer (i.e.—a copolymer the molar ratio of which is 50% or greater ethylene). The more ethylene input to a reactor in a given unit of time, the greater will be the amount of ethylene based copolymer product obtained in that same unit of time. Yet, polymers are designed for a variety of end services and this design constraint dictates the molar percentage of incorporated α-olefin which must be obtained in the targeted copolymer product. The "catalyst reactive ratio ($r_1$)" of a catalyst system defines the property of the system of assimilating an ethylene monomer into a polymer molecule chain in preference to a particular α-olefin comonomer. The larger the $r_1$ number, the greater the preference of the catalyst system for incorporating an ethylene monomer rather than a α-olefin monomer. Thus, to achieve a targeted α-olefin monomer incorporation ($C_\alpha$) in the product polymer, the higher the $r_1$ value of a catalyst system, the larger must be the $C_\alpha/C_2$ molar ratio of monomers used in the reactor, and as the $C_\alpha/C_2$ ratio increases the lower is the production capacity of the reactor.

To achieve a desired level of α-olefin monomer incorporation in a copolymer product, as can be seen, it is often desired to have a catalyst system which can achieve a low molar ratio of $C_\alpha/C_2$, i.e., a catalyst system with a low $r_1$ is desired. For example, with reference to 1-butene, the catalyst systems of this invention wherein the titanium metal compound has a tetramethyl substitute cyclopentadienyl ligand generally exhibit an $r_1$ value of 6 or less, and typically of 5 or less. Thus, with catalyst systems of this invention an e-olefin incorporation of greater than 20 wt. % can be achieved at a $C_\alpha/C_2$ ratio of 2.0 or less, and typically of about 1.6.

In addition to the benefits of increased reactor productivity which, for a copolymer of a targeted α-olefin incorporation level, which a catalyst system of lower $r_1$ values allows, other significant additional benefits ensue from a low $r_1$ value. Recovery of unreacted monomer, particularly α-olefin monomer for later reuse adds significantly to production cost. By use of the catalyst systems identified by this invention, the cost of unreacted α-olefin monomer recovery may be reduced significantly since a smaller quantity of α-olefin monomer can be used to achieve the same target level of α-olefin incorporation.

Further, since it is the ratio of $C_\alpha/C_2$ in the medium wherein polymerization occurs which is critical (i.e., liquid phase, gas phase, or super critical fluid phase, etc.) the low $r_1$ values for the catalyst systems of this invention permit the catalyst systems to be used in a wider variety of polymerization procedures than was heretofore believed to be practically possible. Particularly within this range of possibilities is that of the gas phase polymerization of an ethylene e-olefin copolymer of a greater than heretofore believed possible level of α-olefin incorporation.

Without limiting in any way the scope of the invention, one means for carrying out the process of the present invention for production of a copolymer is as follows: in a stirred-tank reactor liquid α-olefin monomer is introduced, such as 1-butene. The catalyst system is introduced via nozzles in either the vapor or liquid phase. Feed ethylene gas is introduced either into the vapor phase of the reactor, or sparged into the liquid phase as is well known in the art. The reactor contains a liquid phase composed substantially of liquid α-olefin comonomer, together with dissolved ethylene gas, and a vapor phase containing vapors of all monomers. The reactor temperature and pressure may be controlled via reflux of vaporizing α-olefin monomer (autorefrigeration), as well as by cooling coils, jackets, etc. The polymerization rate is controlled by the concentration of catalyst. The ethylene content of the polymer product is determined by the ratio of ethylene to α-olefin comonomer in the reactor, which is controlled by manipulating the relative feed rates of these components to the reactor.

As before noted, a catalyst system wherein the Group IV B transition metal component is titanium has the ability to incorporate high contents of α-olefin comonomers. Accordingly, the selection of the titanium metal component to have the cyclopentadienyl group to be tetramethyl substituted and to have an amido group bridged through its nitrogen atom to the cyclopentadienyl ring wherein the nitrogen of the amido group is bonded through a 1° or 2° carbon atom to an aliphatic or alicyclic hydrocarbyl group, most preferably an alicyclic hydrocarbyl group is another parameter which may be utilized as a control over the α-olefin content of the ethylene-α-olefin copolymer within a reasonable ratio of ethylene to α-olefin comonomer. For reasons already explained, in the production of an ethylene-α-olefin copolymer a molar ratio of ethylene to α-olefin of 2.0 or less is preferred, and a ratio of 1.6 or less is more preferred.

EXAMPLES

In the examples which illustrate the practice of the invention the analytical techniques described below were employed for the analysis of the resulting polyolefin products. Molecular weight determinations for polyolefin products were made by Gel Permeation Chromatography (GPC) according to the following technique. Molecular weights and molecular weight distributions were measured using a Waters 150 gel permeation chromatograph equipped with a differential refractive index (DRI) detector and a Chromatix KMX-6 on-line light scattering photometer. The system was used at 135° C. with 1,2,4-trichlorobenzene as the mobile phase. Shodex (Showa Denko America, Inc.) polystyrene gel columns 802, 803 and 805 were used. This technique is discussed in "Liquid Chromatography of Polymers and Related Materials III", J. Cazes editor, Marcel Dekker, 1981, p. 207, which is incorporated herein by reference. No corrections for column spreading were employed; however, data on generally accepted standards, e.g. National Bureau of Standards Polyethylene 1484 and anionically produced hydrogenated polyisoprenes (an alternating ethylene-propylene copolymer) demonstrated that such corrections on Mw/Mn (=MWD) were less than 0.05 units. Mw/Mn was calculated from elution times. The numerical analyses were performed using the commercially available Beckman/CIS customized LALLS software in conjunction with the standard Gel Permeation package, run on a HP 1000 computer.

The following examples are intended to illustrate specific embodiments of the invention and are not intended to limit the scope of the invention.

All procedures were performed under an inert atmosphere of helium or nitrogen. Solvent choices are often optional, for example, in most cases either pentane or 30–60 petroleum ether can be interchanged. The lithiated amides were prepared from the corresponding amines and either n-BuLi or MeLi. Published methods for preparing $LiHC_5Me_4$ include C. M. Fendrick et a. *Organometallics*, 3, 819 (1984) and F. H. Köhler and K. H. Doll, *Z. Naturforich*, 376, 144 (1982). Other lithiated substituted cyclopentadienyl compounds are typically prepared from the corresponding cyclopentadienyl ligand and n-BuLi or MeLi, or by reaction of MeLi with the proper fulvene. $TiCl_4$, $ZrCl_4$ and $HfCl_4$ were purchased from either Aldrich Chemical Company or Cerac. TiCl4 was typically used in its etherate form. The etherate, $TiCl_4.2Et_2O$, can be prepared by gingerly adding $TiCl_4$ to diethylether. Amines, silanes, substituted and unsubstituted cyclopentadienyl compounds or precursors, and lithium reagents were purchased from Aldrich Chemical Company or Petrarch Systems. Methylalumoxane was supplied by either Sherring or Ethyl Corp.

Further, since the full disclosure of U.S. Application Ser. No. 581,841 has been incorporated herein, the Examples hereof are identified by designations which are consistent with the Example designations of the incorporated application. Examples of the incorporated application relating to the Zr or Hf metal classes of a mono(cyclopentadienyl) transition metal catalyst system are not here repeated (which are Examples A to L) for sake of brevity. Accordingly, not verbatim repeated herein (but incorporated) are Examples A to L, and certain other double letter designated Examples of the incorporated patent. Set forth verbatim herein as repeats of Examples of the incorporated application are Examples AT, FT, IT, JT 40–47, 53–58, 58, 67 and 70.

EXAMPLE AT

Compound AT:
Part 1. $MePhSiCl_2$ (14.9 g, 0.078 mol) was diluted with 250 ml of thf. $Me_4HC_5Li$ (10.0 g, 0.078 mol) was slowly added as a solid. The reaction solution was allowed to stir overnight. The solvent was removed via a vacuum to a cold trap held at −196° C. Petroleum ether was added to precipitate the LiCl. The mixture was filtered through Celite and the pentane was removed from the filtrate. MePhSi(Me$_4$C$_5$H)Cl (20.8 g, 0.075 mol) was isolated as a yellow viscous liquid.

Part 2. LiHN-t-Bu (4.28 g, 0.054 mol) was dissolved in ~100 ml of thf. MePhSi(C$_5$Me$_4$H)Cl (15.0 g, 0.054 mol) was added dropwise. The yellow solution was allowed to stir overnight. The solvent was removed in vacuo. Petroleum ether was added to precipitate the LiCl. The mixture was filtered through Celite, and the filtrate was evaporated. MePhSi(C$_5$Me$_4$H)(NH-t-Bu) (16.6 g, 0.053 mol) was recovered as an extremely viscous liquid.

Part 3. MePhSi(C$_5$Me$_4$H) (NH-t-Bu) (17.2 g, 0.055 mol) was diluted with ~20 ml of ether. n-BuLi (60 ml in hexane, 0.096 mol, 1.6M) was slowly added and the reaction mixture was allowed to stir for ~3 hours. The solvent was removed in vacuo to yield 15.5 g (0.48 mol) of a pale tan solid formulated as Li$_2$[MePhSi(C$_5$Me$_4$) (N-t-Bu)].

Part 4. Li2[MePhSi(C$_5$Me$_4$)(N-t-Bu)] (8.75 g, 0.027 mol) was suspended in ~125 ml of cold ether (−30° C.). TiCl$_4$.2Et$_2$O (9.1 g, 0.027 mol) was slowly added. The reaction was allowed to stir for several hours prior to removing the ether via vacuum. A mixture of toluene and dichloromethane was then added to solubilize the product. The mixture was filtered through Celite to remove the LiCl. The solvent was largely removed via vacuum and petroleum ether was added. The mixture was cooled to maximize product precipitation. The crude product was filtered off and redissolved in toluene. The toluene insolubles were filtered off. The toluene was then reduced in volume and petroleum ether was added. The mixture was cooled to maximize precipitation prior to filtering off 3.34 g (7.76 mmol) of the yellow solid MePhSi(C$_5$Me$_4$)(N-t-Bu)TiCl$_2$.

EXAMPLE FT

Compound FT:

Part 1. (C$_5$Me$_4$H)SiMe$_2$Cl was prepared as described in Example BT for the preparation of compound BT, Part 1.

Part 2. (C$_5$Me$_4$H)SiMe$_2$Cl (5.19 g, 0.029 mol) was slowly added to a solution of LiHNC$_6$H$_{11}$ (2.52 g, 0.024 mol) in ~125 ml of thf. The solution was allowed to stir for several hours. The thf was removed via vacuum and petroleum ether was added to precipitate the LiCl which was filtered off. The solvent was removed from the filtrate via vacuum yielding 6.3 g (0.023 mol) of the yellow liquid, Me$_2$Si(C$_5$Me$_4$H) (HNC$_6$H$_{11}$).

Part 3. Me$_2$Si(C$_5$Me$_4$H) (HNC$_6$H$_{11}$) (6.3 g, 0.023 tool) was diluted with —100 ml of ether. MeLi (33 ml, 1.4M in ether, 0.046 mol) was slowly added and the mixture was allowed to stir for 0.5 hours prior to filtering off the white solid. The solid was washed with ether and vacuum dried. Li[Me$_2$Si(C$_5$Me$_4$)(NC$_6$H$_{11}$)] was isolated in a 5.4 g (0.019 mol) yield.

Part 4. Li$_2$[Me$_2$Si(C$_5$Me$_4$)(NC$_6$H$_{11}$)] (2.57 g, 8.90 mmol) was suspended in ~50 ml of cold ether. TiCl$_4$.2Et$_2$O (3.0 g, 8.9 mmol) was slowly added and the mixture was allowed to stir overnight. The solvent was removed via vacuum and a mixture of toluene and dichloromethane was added. The mixture was filtered through Celite to remove the LiCl byproduct. The solvent was removed from the filtrate and a small portion of toluene was added followed by petroleum ether. The mixture was chilled in order to maximize precipitation. A brown solid was filtered off which was initially dissolved in hot toluene, filtered through Celite, and reduced in volume. Petroleum ether was then added. After refrigeration, an olive green solid was filtered off. This solid was recrystallized twice from dichloromethane and petroleum ether to give a final yield of 0.94 g (2.4 mmol) of the pale olive green solid, Me$_2$Si(C$_5$Me$_4$) (NC$_6$H$_{11}$)TiCl.

EXAMPLE IT

Compound IT:

Part 1. (C$_5$Me$_4$H)SiMe$_2$Cl was prepared as described in Example BT for the preparation of Compound BT, part 1.

Part 2. (C$_5$Me$_4$H)SiMe$_2$Cl (10.0 g, 0.047 mol) was slowly added to a suspension of LiHN-t-Bu (3.68 g, 0.047 mol, ~100 ml thf). The mixture was stirred overnight. The thf was then removed via a vacuum to a cold trap held at −196° C. Petroleum ether was added to precipitate out the LiCl. The mixture was filtered through Celite. The solvent was removed from the filtrate. Me$_2$Si(C$_5$Me$_4$H)(NH-t-Bu) (11.14 g, 0.044 mol) was isolated as a pale yellow liquid.

Part 3. Me$_2$Si(C$_5$Me$_4$H) (NH-t-Bu) (11.14 g, 0.044 mol) was diluted with ~100 ml of ether. MeLi (1.4M, 64 ml, 0.090 mol) was slowly added. The mixture was allowed to stir for ½ hour after the final addition of MeLi. The ether was reduced in volume prior to filtering off the product. The product, [Me$_2$Si(C$_5$Me$_4$)(N-t-Bu)]Li$_2$, was washed with several small portions of ether, then vacuum dried.

Part 4. [Me$_2$Si(C$_5$Me$_4$)(N-t-Bu)Li$_2$ (6.6 g, 0.025 mol) was suspended in cold ether. TiCl$_4$.2Et$_2$O (8.4 g, 0.025 mol) was slowly added and the resulting mixture was allowed to stir overnight. The ether was removed via a vacuum to a cold trap held at −196° C. Methylene chloride was added to precipitate out the LiCl. The mixture was filtered through Celite. The solvent was significantly reduced in volume and petroleum ether was added to precipitate out the product. This mixture was refrigerated prior to filtration in order to maximize precipitation. Me$_2$Si(C$_5$Me$_4$)(N-t-Bu)TiCl$_2$ was isolated (2.1 g, 5.7 mmol).

EXAMPLE JT

Compound JT:

Part 1. (C$_5$Me$_4$H)SiMe$_2$Cl was prepared as described in Example BT for the preparation of Compound Bt, Part 1.

Part 2. (C$_5$Me$_4$H)SiMe$_2$Cl (8.0 g, 0.037 mol) was slowly added to a suspension of LiHNC$_{12}$H$_{23}$ (C$_{12}$H$_{23}$=cyclododecyl, 7.0 g, 0.037 mol, ~80 ml thf). The mixture was stirred overnight. The thf was then removed via a vacuum to a cold trap held at −196° C. Petroleum ether and toluene was added to precipitate out the LiCl. The mixture was filtered through Celite. The solvent was removed from the filtrate. Me$_2$Si(C$_5$Me$_4$H)(NHC$_2$H$_{23}$) (11.8 g, 0.033 mol) was isolated as a pale yellow liquid.

Part 3. Me$_2$Si(C$_5$Me$_4$H) (NHC$_{12}$H$_{23}$) (11.9 g, 0.033 mol) was diluted with ~150 ml of ether. MeLi (1.4M, 47 ml, 0,066 mol) was slowly added. The mixture was allowed to stir for 2 hours after the final addition of MeLi. The ether was reduced in volume prior to filtering off the product. The product, [Me$_2$Si(C$_5$Me$_4$)(NC$_{12}$H$_{23}$)]Li$_2$, was washed with several small portions of ether, then vacuum dried to yield 11.1 g (0,030 mol) of product.

Part 4. [Me$_2$Si(C$_5$Me$_4$) (NC$_{12}$H$_{23}$)]Li$_2$ (3.0 g, 0.008 mol) was suspended in cold ether. TiCl$_4$.2Et2O (2.7 g, 0.008 mol) was slowly added and the resulting mixture was allowed to stir overnight. The ether was removed via a vacuum to a cold trap held at −196° C. Methylene chloride was added to precipitate out the LiCl. The mixture was filtered through Celite. The solvent was significantly reduced in volume and petroleum ether was added to precipitate out the product. This mixture was refrigerated prior to filtration in order to maximize precipitation. The solid collected was recrystallized from methylene chloride and $Me_2Si(C_5Me_4)(NC_{12}H_{23})TiCl_2$ was isolated (1.0 g, 2.1 mmol).

EXAMPLE KT

Compound KT:

Part 1. $(C_5Me_4H)SiMe_2Cl$ was prepared as described in Example A for the preparation of compound A, Part 1.

Part 2. $(C_5Me_4H)SiMe_2Cl$ (6.0 g, 0.0279 mol) was diluted in 200 ml of thf. $LiHNC_{12}H_{25}$ ($C_{12}H_{25}$=n-dodecyl, 5.33 g, 0.0279 ml) was slowly added and the mixture was allowed to stir for 3 hours. The thf was removed in vacuo and 200 ml ether was added.

To this solution, MeLi (1.4M, 34 ml, 0.0476 mol) was slowly added. Upon completion of the reaction, a small amount of $TiCl_4.2Et_2O$ was added to scavenge the excess MeLi. The solution was then cooled to −30° C. and an additional 7.75 g (0,030 mol) of $TiCl_4.2Et_2O$ was added. The mixture was allowed to stir overnight. The solvent was removed and pentane was added. The resulting mixture was filtered through Celite to remove the LiCl. The filtrate was reduced in volume and chilled to induce crystallization of the product. Filtration yielded 4.2 g (0.0087 mol) $Me_2Si(C_5Me_4)(NC_{12}H_{25})TiCl_2$.

EXAMPLE LT

Compound LT:

Part 1. $(C_5Me_4H)SiMe_2Cl$ was prepared as described in Example A for the preparation of compound A, Part 1.

Part 2. $(C_5Me_4H)SiMe_2Cl$ (12.0 g, 0.056 mol) was diluted with 300 ml of thf. $LiHNC_8H_{15}$ ($C_8H_{15}$=cyclooctyl, 742 g, 0.056 mol) was slowly added and the mixture was allowed to stir overnight. The reaction product, $Me_2Si(C_5Me_4H)(HNC_8H_{15})$ was not isolated. The thf was removed and 300 ml of diethyl ether was added. MeLi (1.12M, 105 ml, 0.118 mol) was slowly added to form the dilithiated salt, $Li_2[Me_2Si(C_5Me_4)(NC_8H_{15})]$. This mixture was cooled to −30° C., and $TiCl_4.2Et_2O$ (19.14 g, 0.057 mol) was slowly added. The resulting mixture was allowed to stir overnight. The ether was removed in vacuo, and pentane was added to solubilize the product. The mixture was filtered through Celite to remove the LiCl. The filtrate was reduced in volume and chilled to −40° C. to induce crystallization of the product. Filtration yielded 7.9 g (0.019 mol) of $Me_2Si(C_5Me_4)(NC_8H_{15})TiCl_2$.

EXAMPLE MT

Compound MT:

Part 1. $(C_5Me_4H)SiMe_4Cl$ (6.0 g, 0.028 mol) was diluted with 150 ml of thf. $LiHNC_8H_{17}$ ($C_8H_{17}$=n-octyl, 3.7 g, 0.030 mol) was slowly added. The mixture was allowed to stir overnight. The reaction product, $Me_2Si(C_5Me_4H(HNC_8H_{17})$ was not isolated prior to adding MeLi (2.1M, 35 ml, 0.074 mol) to give $Li_2[Me_2Si(C_5Me_4)(NC_8H_{17})]$. The solvent was removed via vacuum and replaced with diethyl ether, then cooled to −30° C. $TiCl_4.2Et_2O$ (8.46 g, 0.025 mol) was slowly added and the mixture was allowed to stir overnight. The solvent was removed in vacuo and methylene chloride was used to solubilize the product. The solvent mixture was filtered through Celite to remove the LiCl. The filtrate was evaporated down to dryness and pentane was added. The pentane soluble fraction was cooled to −40° C. to induce crystallization of the product. After filtration, $Me_2Si(C_5Me_4)(NC_8H_{17})TiCl_2$ was isolated (1.8 g, 0.0042 mol).

EXAMPLE NT

Compound NT:

Part 1. $(C_5Me_4H)SiMe_2Cl$ was prepared as described in Example A for the preparation of compound A, Part 1.

Part 2. $(C_5Me_4H)SiMe_2Cl$ (6.0 g, 0.028 mol) was diluted in 150 ml of thf. $LiHNC_6H_{13}$ ($C_6H_{13}$=n-hexyl, 2.99 g, 0.028 mol) was slowly added. The mixture was allowed to stir overnight. The thf was removed via vacuum and replaced with diethyl ether. The reaction product $Me_2Si(C_5Me_4H)(HNC_6H_{13})$ was not isolated prior to adding MeLi (1.4M, 45 Ml, 0.063 mol) to give $Li_2[Me_2Si(C_5Me_4)(NC_6H_{13})]$. The resulting mixture was then cooled to −30° C. $TiCl_4.2Et_2O$ (8.6 g, 0.025 mol) was slowly added and the mixture was allowed to stir overnight. The solvent was removed in vacuo and pentane was used to solubilize the product. The solvent mixture was filtered through Celite to remove the LiCl. The filtrate was reduced in volume and cooled to −40° C. to induce crystallization of the product. While crystalline material appeared in the flask at −40° C., upon slight warming, it dissolved back into solution and therefore could not be isolated by filtration. $Me_2Si(C_5Me_4)(NC_6H_{13})TiCl2$ was isolated in an oil form by removing the solvent from the above solution. (4.0 g, 0.010 mol).

EXAMPLE OT

Compound OT:

Part 1. $MePhSi(C_5Me_4H)Cl$ was prepared as described in Example AT for the preparation of compound AT, Part 1.

Part 2. $MePhSi(C_5Me_4H)Cl$ (6.0 g, 0.022 mol) was diluted with ether. LiHN-s-Bu (1.7 g, 0.022 mol) was slowly added and the mixture was allowed to stir overnight. The solvent was removed and a mixture of toluene and petroleum ether was added. This mixture was filtered through Celite to remove the LiCl. The solvent was removed via vacuum leaving behind the viscous liquid, $MePhSi(C_5Me_4H)(HN-s-Bu)$. To this liquid which was diluted with ether, 28 ml (0.039 mol 1.4M in ether) MeLi was slowly added. After stirring overnight, a small portion of $TiCl_4.2Et_2O$ (total of 5.86 g, 0.017 mol) was slowly added and the mixture was allowed to stir overnight. The solvent was removed via vacuum, dichloromethane was added and the mixture was filtered through Celite. The filtrate was evaporated down producing a brown solid. Petroleum ether was added and the mixture was filtered. The brown solid remaining on the filter stick was discarded and the filtrate was reduced in volume and refrigerated to maximize precipitation. After filtration and washing with cold aliquots of petroleum ether, a dark mustard yellow solid was isolated and identified as $MephSi(C_5Me_4)(N-s-Bu)TiCl2$ (2.1 g, 4.9 mmol).

EXAMPLE PT

Compound PT:

Part 1. $MephSi(C_5Me_4H)Cl$ was prepared as described in Example AT for the preparation of compound AT, Part 1.

Part 2. $MephSi(C_5Me_4H)Cl$ (6.0 g, 0.022 mol) was diluted with ether. LiHN-n-Bu (1.7 g, 0.022 mol) was slowly added and the mixture was allowed to stir overnight. The solvent was removed via vacuum and a mixture of toluene and petroleum ether was added. This was filtered through Celite to remove the LiCl. The solvent was removed from the filtrate leaving behind a viscous yellow liquid which was diluted with ether. To this, 28 ml of MeLi (1.4M in ether, 0.038 mol) was added and the mixture was allowed to stir overnight. A small portion of TiCl$_4$.2Et$_2$O (total of 5.7 g, 0.017 mol) was slowly added. In spite of the slow addition, the highly exothermic reaction bumped, thus some product loss occurred at this point in the reaction. The remaining mixture was stirred overnight. The solvent was then removed via vacuum. Dichloromethane was added and the mixture was filtered through Celite to remove the LiCl. The solvent was removed and petroleum ether was added. The mixture was refrigerated to maximize precipitation. Filtration produced a yellow-brown solid which was recrystallized from petroleum ether. The final filtration produced 2.0 g (4.6 mmol) of MePhSi(Me$_4$C$_5$)(N-n-Bu)TiCl$_2$.

EXAMPLE QT

Compound QT:

Part 1. (C$_5$Me$_4$H)SiMe$_2$Cl was prepared as described in Example A for the preparation of compound A, Part 1.

Part 2. (C$_5$Me$_4$H)SiMe$_2$Cl (9.0 g, 0.042 mol) was diluted in ether. LiHn-s-Bu (3.31 g, 0.042 mol) was slowly added and the mixture was allowed to stir overnight. The solvent was removed via vacuum and petroleum ether was added. This mixture was filtered through Celite to remove the LiCl. The solvent was removed from the filtrate leaving behind the pale yellow liquid, Me$_2$Si(C$_5$Me$_4$H) (HN-s-Bu) (10.0 g, 0.040 mol).

Part 3. Me$_2$Si(C$_5$Me$_4$H) (HN-s-Bu) (10.0 g, 0.040 mol) was diluted with ether. MeLi (58 ml, 1.4M in ether, 0.081 mol) was added and the mixture was allowed to stir overnight. The solvent was reduced in volume and the white solid was filtered off and washed with small portions of ether. Li$_2$[Me$_2$Si(C$_5$Me$_4$)(N-s-Bu)] (10.1 g, 0.038 mol) was isolated after vacuum drying.

Part 4. Li$_2$[Me$_2$Si(C$_5$Me$_4$)(N-s-Bu)] (7.0 g, 0.027 mol) was suspended in cold ether. TiCl$_4$.2Et$_2$O (8.98 g, 0.027 mol) was slowly added and the mixture was allowed to stir overnight. The solvent was removed via vacuum and dichloromethane was added. The mixture was filtered through Celite to remove the LiCl. The filtrate was reduced in volume and petroleum ether was added. This mixture was refrigerated to maximize precipitation prior to filtering off the olive green solid. The solid was recrystallized from dichloromethane and petroleum ether yielding 2.4 g (6.5 mol) of the yellow solid, Me$_2$Si(C$_5$Me$_4$)(N-s-Bu)TiCl$_2$.

EXAMPLE RT

Compound RT:

Part 1. (C$_5$Me$_4$H)SiMe$_2$Cl was prepared as described in Example A for the preparation of compound A, Part 1.

Part 2. (C$_5$Me$_4$H)SiMe$_2$Cl (8.0 g, 0.037 mol) was diluted with ether. LiHN-n-Bu (2.95 g, 0.037 mol) was slowly added and the mixture was allowed to stir overnight. The solvent was removed via vacuum and petroleum ether was added. The mixture was filtered through Celite to remove the LiCl. The solvent was removed from the filtrate leaving behind the yellow liquid, Me$_2$Si(C$_5$Me$_4$H)(HN-n-Bu) (8.6 g, 0.034 mol).

Part 3. Me$_2$Si(C$_5$Me$_4$H)(HN-n-Bu) (8.6 g, 0.034 mol) was diluted with ether. MeLi (50 ml, 1.4M in ether, 0.070 mol) was slowly added and the mixture was allowed to stir for two hours. The solvent was removed leaving behind 10.2 g (0.035 mol) of the yellow solid, Li$_2$[Me$_2$Si(C$_5$Me$_4$) (N-n-Bu)].⅓Et$_2$O.

Part 4. Li$_2$[Me$_2$Si(C$_5$Me$_4$)(N-n-Bu)].⅓Et$_2$O (6.0 g, 0.021 mol) was suspended in cold ether. TiCl$_4$.2Et$_2$O (7.04 g, 0.0212 mol) was slowly added and the mixture was allowed to stir overnight. The solvent was removed and dichloromethane was added. The mixture was filtered through Celite to remove the LiCl. The filtrate was reduced in volume and petroleum ether was added. The mixture was refrigerated to maximize precipitation prior to filtering off a mixture of dark powder and yellow crystals. The material was redissolved in a mixture of dichloromethane and toluene. A small portion of petroleum ether was added and the brown precipitate was filtered off and discarded. The filtrate was reduced in volume, additional petroleum ether was added and the mixture was placed back in the refrigerator. Later, 3.65 g of the maize yellow solid, Me$_2$Si(C$_5$Me$_4$)(N-n-Bu)TiCl$_2$ was filtered off.

EXAMPLE ST

Compound ST:

Part 1. Me$_2$SiCl$_2$ (210 ml, 1.25 mol) was diluted with a mixture of ether and thf. LiMeC$_5$H$_4$ (25 g, 0.29 mol) was slowly added, and the resulting mixture was allowed to stir for a few hours, after which time the solvent was removed in vacuo. Pentane was added to precipitate the LiCl, and the mixture was filtered through Celite. The pentane was removed from the filtrate leaving behind a pale yellow liquid, Me$_2$Si(MeC$_5$H$_4$)Cl.

Part 2. Me$_2$Si(MeC$_5$H$_4$)Cl (10.0 g, 0.058 mol) was diluted with a mixture of ether and thf. To this, LiHNC$_{12}$H$_{23}$ (11.0 g, 0.058 mol) was slowly added. The mixture was allowed to stir overnight. The solvent was removed via vacuum and toluene and pentane were added to precipitate the LiCl. The solvent was removed from the filtrate leaving behind a pale yellow liquid, Me$_2$Si(MeC$_5$H$_4$)(HNC$_{12}$H$_{23}$) (18.4 g, 0.058 mol).

Part 3. Me$_2$Si(MeC5H4)(HNC12H23) (18.4 g, 0.058 mol) was diluted in ether. MeLi (1.4M in ether, 82 ml, 0.115 mol) was slowly added. The reaction was allowed to stir for several hours before reducing the mixture in volume and then filtering off the white solid, Li$_2$[Me$_2$Si(MeC$_5$H$_3$)(NC$_{12}$H$_{23}$)] (14.3 g, 0.043 mol).

Part 4. Li$_2$[Me$_2$Si(MeC$_5$H$_3$)(NC$_{12}$H$_{23}$)](7.7 g, 0.023 mol) was suspended in cold ether. TiCl$_4$.2Et$_2$O (7.8 g, 0.023 mol) was slowly added and the mixture was allowed to stir overnight. The solvent was removed via vacuum. Dichloromethane was added and the mixture was filtered through Celite. The dichloromethane was reduced in volume and petroleum ether was added to maximize precipitation. This mixture was then refrigerated for a short period of time prior to filtering off a yellow/green solid identified as Me$_2$Si(MeC$_5$H$_3$)(NC$_{12}$H$_{23}$)TiCl$_2$ (5.87 g, 0.013 mol).

EXAMPLE TT

Compound TT:

Part 1. Me$_2$SiCl$_2$ (7.5 ml, 0.062 mol) was diluted with ~30 ml of thf. A t-BuH$_4$C$_5$Li solution (7.29 g, 0,057 mol -100 ml of thf) was slowly added, and the resulting mixture was allowed to stir overnight. The thf was removed in vacuo. Pentane was added to precipitate the LiCl, and the mixture was filtered through Celite. The pentane was removed from the filtrate leaving behind a pale yellow liquid, Me$_2$Si(t-BuC$_5$H$_4$)Cl (10.4 g, 0.048 mol).

Part 2. Me$_2$Si(t-BuC$_5$H$_4$)Cl (8.0 g, 0.037 mol) was diluted with thf. To this, LiHNC$_{12}$H$_{23}$ (7.0 g, 0.037 mol) was slowly added. The mixture was allowed to stir overnight. The solvent was removed via vacuum and toluene was added to precipitate the LiCl. The toluene was removed from the filtrate leaving behind a pale yellow liquid, $Me_2Si(t-BuC_5H_4)(HNC_{12}H_{23})$ (12.7 g, 0.035 mol).

Part 3. $Me_2Si(t-BuC_5H_4)(HNC_{12}H_{23})$ (12.7 g, 0.035 mol) was diluted with ether. To this, MeLi (1.4M in ether, 50 ml, 0.070 mol) was slowly added. This was allowed to stir for two hours prior to removing the solvent via vacuum. The product, $Li_2[Me_2Si(t-BuC_5H_3)(NC_{12}H_{23})]$ (11.1 g, 0.030 mol) was isolated.

Part 4. $Li_2[Me_2Si(t-BuC_5H_3)(NC_{12}H_{23})]$ (10.9 g, 0.029 mol) was suspended in cold ether. $TiCl_4 \cdot 2Et_2O$ (9.9 g, 0.029 mol) was slowly added and the mixture was allowed to stir overnight. The solvent was removed via vacuum. Dichloromethane was added and the mixture was filtered through Celite. The solvent was removed and pentane was added. The product is completely soluble in pentane. This solution was passed through a column containing a top layer of silica and a bottom layer of Celite. The filtrate was then evaporated down to an olive green colored solid identified as $Me_2Si(t-BuC_5H_3)(NC_{12}H_{23})TiCl_2$ (5.27 g, 0.011 mol).

EXAMPLE UT

Compound UT $Me_2Si(C_5Me_4)(NC_{12}H_{23})TiMe_2$ was prepared by adding a stoichiometric amount of MeLi (1.4M in ether) to $Me_2Si(C_5Me_4)(NC_{12}H_{23})TiCl_2$ (Compound JT from Example JT) suspended in ether. The white solid recrystallized from toluene and petroleum ether was isolated in a 57% yield.

EXAMPLE 40

Polymerization—Compound AT

The polymerization run was performed in a 1-liter autoclave reactor equipped with a paddle stirrer, an external water jacket for temperature control, a regulated supply of dry nitrogen, ethylene, propylene, 1-butene and hexane, and a septum inlet for introduction of other solvents or comonomers, transition metal compound and alumoxane solutions. The reactor was dried and degassed thoroughly prior to use. A typical run consisted of injecting 400 ml of toluene, 5 ml of 1.0M MAO, 0,206 mg compound AT (0.2 ml of a 10.3 mg in 10 ml of toluene solution) into the reactor. The reactor was then heated to 80° C. and the ethylene (60 psi) was introduced into the system. The polymerization reaction was limited to 30 minutes. The reaction was ceased by rapidly cooling and venting the system. The solvent was evaporated off of the polymer by a stream of nitrogen. Polyethylene was recovered (11.8 g, MW=279,700, MWD=2,676).

EXAMPLE 41

Polymerization—Compound AT

Using the same reactor design and general procedure as described in Example 40, 400 ml of toluene, 5.0 ml of 1.0M MAO, and 0.2 ml of a preactivated compound AT solution (10.3 mg of compound AT dissolved in 9.5 ml of toluene and 0.5 ml of 1.0M MAO) were added to the reactor. The reactor was heated to 80° C., the ethylene was introduced (60 psi), and the reaction was allowed to run for 30 minutes, followed by rapidly cooling and venting the system. After evaporation of the solvent, 14.5 g of polyethylene was recovered (MW=406,100, MWD=2.486).

EXAMPLE 42

Polymerization—Compound AT

Using the same reactor design and general procedure described in Example 40, 300 ml of toluene, 100 ml of 1-hexene, 7.0 ml of 1.0M MAO, and 1.03 mg of compound AT (1.0 ml of 10.3 mg in 10 ml of toluene solution) were added to the reactor. The reactor was heated at 80° C., the ethylene was introduced (65 psi), and the reaction was allowed to run for 10 minutes, followed by rapidly cooling and venting the system. After evaporation of the toluene, 48.6 g of an ethylene-1-hexene copolymer was recovered (MW=98,500, MWD=1.745, 117 SCB/1000 C by $^{13}C$ NMR).

EXAMPLE 43

Polymerization—Compound AT

Using the same reactor design and general procedure described in Example 40, 375 ml of toluene, 25 ml of 1-hexene, 7.0 ml of 1.0M MAO, and 1.03 mg of compound AT (1.0 ml of a 10.3 mg in 10 ml of toluene solution) were added to the reactor. The reactor was heated at 80° C., the ethylene was introduced (65 psi), and the reaction was allowed to run for 10 minutes, followed by rapidly cooling and venting the system. After evaporation of the toluene, 29.2 g of an ethylene-1-hexene copolymer was recovered (MW=129,800, MWD=2.557, 53.0 SCB/1000 C by $^{13}C$ NMR).

EXAMPLE 44

Polymerization—Compound AT

Using the same reactor design and general procedure described in Example 40, 375 ml of toluene, 25 ml of 1-hexene, 7.0 ml of 1.0M MAO, and 1.03 mg of compound AT (1.0 ml of 10.3 mg in 10 ml of toluene solution) were added to the reactor. The reactor was heated at 50° C., the ethylene was introduced (65 psi), and the reaction was allowed to run for 10 minutes, followed by rapidly cooling and venting the system. After evaporation of the toluene, 15.0 g of an ethylene-1-hexene copolymer was recovered (MW=310,000, MWD=2,579, 47.2 SCB/1000 C by $^{13}C$ NMR).

EXAMPLE 45

Polymerization—Compound AT

Using the same reactor design and general procedure described in Example 40, 300 ml of toluene, 100 ml of propylene, 7.0 ml of 1.0M MAO, and 2.06 mg of compound AT (2.0 ml of a 10.3 mg in 10 ml of toluene solution) were added to the reactor. The reactor was heated at 80° C., the ethylene was introduced (65 psi), and the reaction was allowed to run for 10 minutes, followed by rapidly cooling and venting the system. After evaporation of the toluene, 46.0 g of an ethylene-propylene copolymer was recovered (MW=110,200, MWD=5.489, 20 wt% ethylene by IR).

EXAMPLE 46

Polymerization—Compound AT

Using the same reactor design and general procedure described in Example 40, 300 ml of toluene, 100 ml of 1-butene, 7.0 ml of 1.0M MAO, and 1.03 mg of compound AT (1.0 ml of 10.3 mg in 10 ml of toluene solution) were added to the reactor. The reactor was heated at 80° C., the ethylene was introduced (65 psi), and the reaction was allowed to run for 10 minutes, followed by rapidly cooling and venting the system. After evaporation of the toluene, 35.1 g of an ethylene-1-butene copolymer was recovered (MW=94,400, MWD=2.405, 165 SCB/1000 C by $^{13}$C NMR).

EXAMPLE 47

Polymerization—Compound AT

Using the same reactor design and general procedure described in Example 40, 300 ml of toluene, 100 ml of 1-octene, 7.0 ml of 1.0M MAO, and 1.04 mg of compound AT (1.0 ml of a 10.4 mg in 10 ml of toluene solution) were added to the reactor. The reactor was heated at 80° C., the ethylene was introduced (65 psi), and the reaction was allowed to run for 10 minutes, followed by rapidly cooling and venting the system. After evaporation of the toluene, 30.6 g of an ethylene-1-octene copolymer was recovered (MW=73,100, MWD=2.552, 77.7 SCB/1000 C by $^{13}$C NMR).

EXAMPLE 53

Polymerization—Compound AT

The polymerization was performed in a stirred 100 ml stainless steel autoclave which was equipped to perform polymerizations at temperatures up to 300° C. and pressures up to 2500 bar. The reactor was evacuated, purged with nitrogen, purged with ethylene and heated to 200° C. 1-hexene (75 ml) was added to the reactor under ethylene pressure. A stock solution of compound AT was prepared by dissolving 6.5 mg of compound AT in 12.5 ml of toluene. The test solution was prepared by adding 1.0 ml of the compound AT stock solution to 1.9 ml of 1.0M MAO solution, followed by 7.1 ml of toluene. The test solution (0.43 ml) was transferred by nitrogen pressure into a constant-volume injection tube. The autoclave was pressurized with ethylene to 1748 bar and was stirred at 1800 RPM. The test solution was injected into the autoclave with excess pressure, at which time a temperature rise of 16° C. was observed. The temperature and pressure were recorded continuously for 120 seconds, at which time the contents of the autoclave were rapidly vented into a receiving vessel. The reactor was washed with xylene to recover any polymer remaining within. These washings were combined with the polymer released when the reactor was vented. Precipitation of the polymer from the mixture by addition of acetone yielded 2.7 g of polymer (MW=64,000, MWD=3.16, 14.7 SCB/1000 C by IR).

EXAMPLE 54

Polymerization—Compound AT

For this Example a stirred 1 L steel autoclave reaction vessel which was equipped to perform continuous Ziegler polymerization reactions at pressures to 2500 bar and temperatures up to 300° C. was used. The reaction system was supplied with a thermocouple and pressure transducer to measure temperature and pressure continuously, and with means to supply continuously purified compressed ethylene and 1-butene (or propylene). Equipment for continuously introducing a measured flow of catalysts solution, and equipment for rapidly venting and quenching the reaction, and of collecting the polymer product were also a part of the reaction system. The polymerization was performed with a molar ratio of ethylene to 1-butene of 1.6 without the addition of a solvent. The temperature of the cleaned reactor containing ethylene and 1-butene was equilibrated at the desired reaction temperature of 180° C. The catalyst solution was prepared by mixing 0.888 g of solid compound AT with 0.67 L of a 30 wt% methylalumoxane solution in 4.3 L of toluene in an inert atmosphere. This catalyst solution was continuously fed by a high pressure pump into the reactor at a rate of 0.56 L/hr which resulted in a temperature of 180° C. in the reactor. During this run, ethylene and 1-butene were pressured into the autoclave at a total pressure of 1300 bar. The reactor contents were stirred at 1000 RPM. The yield of polymer products was 3.9 kg/hr of an ethylene-1-butene copolymer which had a weight average molecular weight of 50,200, a molecular weight distribution of 2.36 and 60.1 SCB/1000 C as measured by $^{13}$C NMR.

EXAMPLE 55

Polymerization—Compound AT

Using the same reactor design as described in Example 54, and using a molar ratio of ethylene to propylene of 2.6 without the addition of a solvent, the temperature of a cleaned reactor containing ethylene and propylene was equilibrated at the desired reaction temperature of 140° C. The catalyst solution was prepared by mixing 0.779 g of solid compound AT with 0.5 L of a 30 wt% methylalumoxane solution in 24.5 L of toluene in an inert atmosphere. This catalyst solution was continuously fed by a high pressure pump into the reactor at a rate of 0.9 L/hr which resulted in a temperature of 140° C. in the reactor. During this run, ethylene and propylene were pressured into the autoclave at a total pressure of 2200 bar. The reactor contents were stirred at 1000 RPM. The yield of polymer product was 2.3 kg/hr of an ethylene-propylene copolymer which had a weight average molecular weight of 102,700, a molecular weight distribution of 2.208 and density of 0.863 g/cc.

EXAMPLE 56

Polymerization—Compound FT

Using the same reactor design as described in Example 54, and using a molar ratio of ethylene to 1-butene of 1.6 without the addition of a solvent. The temperature of the cleaned reactor containing ethylene and 1-butene was equilibrated at the desired reaction temperature of 180° C. The catalyst solution was prepared by mixing 0.859 g of solid FT with 30 wt% methylalumoxane solution and toluene such that the catalyst concentration was 0.162 g/L with an Al/M molar ratio of 1200. The preparation was done under an inert atmosphere. This catalyst solution was continuously fed by a high pressure pump into the reactor at a rate of 1.15 L/hr which resulted in a temperature of 180° C. in the reactor. During this run, ethylene and 1-butene were pressured into the autoclave at a total pressure of 1300. The reactor contents were stirred at 1000 RPM. The yield of polymer product was 3.9 kg/hr of an ethylene-1-butene copolymer which had a weight average molecular weight of 61,400, a molecular weight distribution of 2.607 and 104.8 SCB/1000 C by $^{13}$C NMR.

EXAMPLE 58

Polymerization—Compound AT

Using the same reactor design as described in Example 54, and using a molar ratio of ethylene to 1-butene of 1.6 without the addition of a solvent, the temperature of the cleaned reactor containing ethylene and 1-butene was equilibrated at the desired reaction temperature of 170° C. The catalyst solution was prepared by mixing 0.925 g of solid compound AT with 2 L of a 10 wt % methylalumoxane solution in 8 L of toluene in an inert atmosphere. This catalyst solution was continuously fed by a high pressure pump into the reactor at a rate of 0.28 L/hr which resulted in a temperature of 170° C. in the reactor. During this run, ethylene and 1-butene were pressured into the autoclave at a total pressure of 1300 bar. The reactor contents were stirred at 1000 RPM. The yield of polymer product was 3.7 kg/hr of an ethylene-1-butene copolymer which had a weight average molecular weight of 69,500, a molecular weight distribution of 2.049 and 35.7 SCB/1000 C by 13C NRM.

EXAMPLE 67

Polymerization—Compound IT

Using the same reactor design as described in Example 54, and using a molar ratio of ethylene to 1-butene of 1.6 without the addition of a solvent, the temperature of the cleaned reactor containing ethylene and 1-butene was equilibrated at the desired reaction temperature of 180° C. The catalyst solution was prepared by mixing 1.94 g of solid compound IT with 30 wt % methylalumoxane solution and toluene such that the catalyst concentration was 0.388 g/L and the Al/M molar ratio was 600. The preparation was done under an inert atmosphere. This catalyst solution was continuously fed by a high pressure pump into the reactor at a rate of 0.42 L/hr which resulted in a temperature of 180° C. in the reactor. During this run, ethylene and 1-butene were pressured into the autoclave at a total pressure of 1300 bar. The reactor contents were stirred at 1000 RPM. The yield of polymer product was 3.9 kg/hr of an ethylene-1-butene copolymer which had a weight average molecular weight of 50,000, 1 molecular weight distribution of 2.467 and 69 SCB/1000C as measured by $^1$H NMR.

EXAMPLE 70

Polymerization—Compound JT

Using the same reactor design as described in Example 54, and using a molar ratio of ethylene to 1-butene of 1.6 without the addition of a solvent, the temperature of the cleaned reactor containing ethylene and 1-butene was equilibrated at the desired reaction temperature of 180° C. The catalyst solution was prepared by mixing 1.78 g of solid Compound JT with 30 wt % methylalumoxane solution and toluene such that the catalyst concentration was 0.318 g/L and the Al/M molar ratio was 1400. The preparation was done under an inert atmosphere. This catalyst solution was continuously fed by a high pressure pump into the reactor at a rate of 0.55 L/hr which resulted in a temperature of 180° C. in the reactor. During this run, ethylene and 1-butene were pressured into the autoclave at a total pressure of 1300 bar. The reactor contents were stirred at 1000 RPM. The yield of polymer product was 3.9 kg/hr of an ethylene-1-butene copolymer which had a weight average molecular weight of 72,600, a molecular weight distribution of 2.385 and 110 SCB/1000 C as measured by $^1$H NMR.

EXAMPLES 71–86

Each of the compounds of Examples KT through TT were used to prepare an ethylene-1-butene copolymer. The polymerization reactions were carried out in the same reactor design as described in Example 54. With the sole exception of Example 83, all polymerizations were carried out using a molar ratio of 1-butene to ethylene of 1.6 without the addition of a solvent. In Example 83 a 1-butene to ethylene ratio of 2.0 was used. The temperature of the cleaned reactor containing ethylene and 1-butene was equilibrated at the desired reaction temperature of 180° C.

The catalyst solution was prepared by mixing a specified amount of solid transition metal component with a 30 weight percent methylalumoxane solution and this catalyst solution was then further diluted in toluene under an inert atmosphere. This catalyst solution was continuously fed by a high pressure pump into the reactor at a rate which resulted in the desired reactor temperature of 180° C., which was the polymerization temperature of all examples. The reactor contents were stirred at 1000 RPM and a reactor mass flow rate of 40 kg/g was used for all examples. The reactor pressure was maintained at 1300 bar and no hydrogen was supplied to the reactor. Exact run conditions including catalyst preparation [transition metal component (TMC) and amount (g), methylalumoxane (MAO) volume used (L), total volume of catalyst solution (L) and concentration (g TMC/L) and (g MAO/L)], catalyst feed rate (L/hr), polymer production rate (kg polymer/hr), molar Al/M ratio, productivity (kg polymer/g catalyst) and polymer characteristics including weight average MW (Daltons), molecular weight distribution (MW/MN), melt index g/10 minute at 190° C.), weight percent comonomer (determined by $^1$H NMR or $^{13}$C NMR), and catalyst reactivity ratios ($r_1$) are collected in Table 1.

By appropriate selection of (1) Group IV B transition metal component for use in the catalyst system; (2) the type and amount of alumoxane used; (3) the polymerization diluent type and volume; (4) reaction temperature; and (5) reaction pressure, one can tailor the product polymer to the weight average molecular weight value desired while still maintaining the molecular weight distribution to a value below about 4.0.

The above polymerization reactions can be repeated utilizing a non-coordinating compatible anion activator compound in place of the alumoxane so long as the Q ligands are compatible therewith, e.g. Q is not an alkoxide or halide. More specifically, Q is hydride or a hydrocarbyl radical, preferably a methyl radical. By appropriate selection of (1) Group IV B transition metal component for use in the catalyst system; (2) the type of non-coordinating anion used; (3) the polymerization diluent type and volume; (4) reaction temperature; and (5) reaction pressure, one can tailor the product polymer to the weight average molecular weight desired while controlling the molecular weight distribution. The following example illustrates one such polymerization.

EXAMPLE AS

An ionic catalyst was prepared by dissolving 50 ml of dimethylsilyl(cyclododecylamido)tetramethylcyclopentadienyltitanium dimethyl and 25 mg N,N-dimethylanilinium tetrakis(pentafluorophenyl)boron in 10 ml toluene. Dry, oxygen-free hexane (400 ml) was added to a 1 liter stainless steel autoclave which had been previously flushed with nitrogen. Under nitrogen, a hexane solution (2 ml) containing 0.25% triisoprenylaluminum was transferred into the autoclave by means of a double-ended needle, followed by 4 ml of the catalyst solution. The ratio of titanium containing catalyst to boron containing activator was 3.7. The solution in the autoclave was heated to 80° C. and 4.42 atmospheres of ethylene (0.228 moles) were introduced. Polymerization was carried out for 0.1 hours, after which time the autoclave was vented and opened. The yield of polyethylene was 2.1 grams. This corresponds to productivity of 61 kg polymer/mole activator atmosphere hour, or 269 kg polymer/mole activator hour.

EXAMPLE AT

An ionic catalyst was prepared and utilized substantially as described in Example AS except that dimethlsilyl(N-t- butylamido)tetramethylcyclopentadienyltitanium dimethyl was substituted for dimethylsilyl(cyclododecylamido) tetramethylcyclopentadienyltitanium dimethyl.

The preferred polymerization diluents for practice of the process of the invention are aromatic diluents, such as toluene, or alkanes, such as hexane.

From the above examples, particularly as collected in Table 1, it appears that for a catalyst system wherein the Group IV B transition metal component is a titanium species of the following structure:

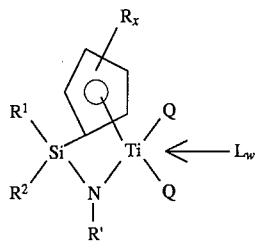

Formula VII the nature of the R' group dramatically influence the catalytic properties of the system. For production of ethylene-α-olefin copolymers of greatest comonomer content, at a selected ethylene to α-olefin monomer ratio, R' is preferably a non-aromatic substituent, such as an alkyl or cycloalkyl substituent preferably bearing a primary or secondary carbon atom attached to the nitrogen atom.

Further, from the above data, the nature of the Cp ligand structure of a Ti metal component may be seen to influence the properties of the catalyst system. Those Cp ligands which are not too sterically hindered and which contain good electron donor groups, for example the $Me_4C_5$ ligand, are preferred.

From the standpoint of having a catalyst system of high productivity which is capable of producing an ethylene-α-olefin copolymer of high molecular weight and high comonomer incorporation, the most preferred transition metal compound for the catalyst system is of the following structure:

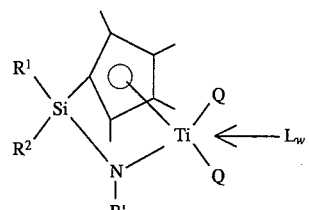

Formula VIII wherein $R^1$ and $R^2$ are alkyl radicals having 1 to 6 carbon atoms, each Q is chlorine or methyl, and R' is an aliphatic or alicyclic hydrocarbyl having from 1 to 20 carbon atoms, preferably 3 to 20 carbon atoms.

The resins that are prepared in accordance with this invention can be used to make a variety of products including films and fibers.

The invention has been described with reference to its preferred embodiments. Those of ordinary skill in the art may, upon reading this disclosure, appreciate changes or modifications which do not depart from the scope and spirit of the invention as described above or claimed hereafter.

TABLE 1

| | Ex. # | TMC (g) | MMO (L) | Total Vol (L) | TMC (g/L) | NAO (g/L) | Feed Rate (L/hr) | Production Rate (kg/hr) | Al/N |
|---|---|---|---|---|---|---|---|---|---|
| JT | 71 | 0.540 | 0.4 | 10 | 0.0540 | 10.4 | 1.75 | 5.1 | 1595 |
| KT | 72 | 2.259 | 1.8 | 6 | 0.3765 | 78.3 | 0.51 | 3.9 | 1723 |
| LT | 73 | 1.480 | 1.2 | 8 | 0.1850 | 39.2 | 0.46 | 4.0 | 1541 |
| MT | 74 | 1.366 | 1.0 | 6 | 0.2277 | 43.5 | 0.58 | 4.0 | 1398 |
| FT | 75 | 0.059 | 0.6 | 5.3 | 0.1620 | 29.5 | 1.14 | 4.2 | 1239 |
| WT | 76 | 1.441 | 1.2 | 8 | 0.1801 | 39.2 | 1.51 | 4.4 | 1485 |
| AT | 77 | 0.888 | 0.7 | 5 | 0.1776 | 35.0 | 0.56 | 4.35 | 1461 |
| DT | 78 | 1.934 | 1.3 | 6 | 0.3223 | 54.4 | 0.62 | 4.3 | 1252 |
| PT | 79 | 1.900 | 1.3 | 6 | 0.3167 | 54.4 | 0.96 | 3.75 | 1274 |
| IT | 80 | 0.878 | 0.8 | 10 | 0.0878 | 19.6 | 0.84 | 4.3 | 1416 |
| QT | 81 | 0.953 | 0.9 | 10 | 0.0953 | 23.5 | 1.32 | 4.9 | 1565 |
| RT | 82 | 0.885 | 0.9 | 10 | 0.0885 | 23.5 | 1.68 | 4.65 | 1685 |
| JT | 83 | 1.494 | 0.5 | 10 | 0.1494 | 13.1 | 1.02 | 3.9 | 721 |
| ST | 84 | 3.053 | 1.0 | 12 | 0.2540 | 21.8 | 0.51 | 2.9 | 643 |
| TT | 85 | 3.043 | 1.0 | 18 | 0.1690 | 14.5 | 1.11 | 2.6 | 708 |
| UT | 86 | 1.566 | 1.0 | 8 | 0.3132 | 52.2 | 0.35 | 5.0 | 1258 |

| | TMC Productivity (kg/g) | Catalyst Productivity (kg/g) | MM | MMD | NI | Wt % C4 | Method | r1 |
|---|---|---|---|---|---|---|---|---|
| JT | 54 | 0.20 | 63,600 | 2.363 | 11.3 | 42.0 | 1 MMMR | 4.4 |
| KT | 20 | 0.10 | 84,100 | 4.775 | 3.3 | 40.8 | 1 MMMR | 4.7 |
| LT | 48 | 0.22 | 72,700 | 3.610 | 7.9 | 42.0 | 1 MMMR | 4.4 |
| MT | 31 | 0.16 | 78,300 | 4.601 | 5.0 | 40.0 | 1 MMMR | 4.7 |
| FT | 23 | 0.12 | 61,400 | 2.607 | 13.2 | 41.9 | 13 CMMR | 4.4 |
| WT | 16 | 0.07 | 85,400 | 3.971 | 3.6 | 44.0 | 1 MMMR | 4.1 |
| AT | 44 | 0.22 | 50,200 | 2.360 | 19 | 24.0 | 13 CMMR | 10 |
| DT | 22 | 0.13 | 64,600 | 2.494 | 8.1 | 43.6 | 13 CMMR | 4.1 |
| PT | 12 | 0.07 | 71,200 | 2.259 | 3.8 | 41.1 | 13 CMMR | 4.6 |
| IT | 59 | 0.26 | 63,600 | 2.751 | 6.6 | 32.4 | 1 MMMR | 6.7 |
| QT | 39 | 0.16 | 64,500 | 2.342 | 10 | 42.8 | 1 MMMR | 4.3 |
| RT | 31 | 0.12 | 71,100 | 2.262 | 0.8 | 40.0 | 1 MMMR | 4.0 |
| JT | 26 | 0.29 | 70,200 | 3.617 | 5.2 | 40.0 | 1 MMMR | 4.6 |

TABLE 1-continued

| | | | | | | | | |
|---|---|---|---|---|---|---|---|---|
| ST | 22 | 0.26 | 60,900 | 2.183 | 8.5 | 17.62 | 13 CMMR | 15.0 |
| TT | 14 | 0.16 | 53,900 | 2.208 | 13.8 | 17.38 | 13 CMMR | 15.2 |
| UT | 46 | 0.27 | 70,200 | 2.441 | 4.6 | 46.4 | 13 CMMR | 3.7 |

We claim:

1. A compound of the formula:

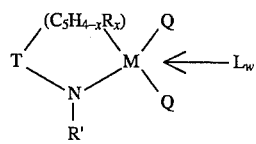

Formula I wherein:

M is Zr, Hf or Ti;

($C_5H_{4-x}R_x$) is a cyclopentadienyl ring which is substituted with from zero to four substituent groups R, "x" is 0, 1, 2, 3, or 4 denoting the degree of substitution, and each substituent group R is, independently, a radical selected from a group consisting of $C_1$–$C_{20}$ hydrocarbyl radicals, substituted $C_1$–$C_{20}$ hydrocarbyl radicals wherein one or more hydrogen atoms is replaced by a halogen radical, an amido radical, a phosphido radical, and alkoxy radical, $C_1$–$C_{20}$ hydrocarbyl-substituted metalloid radicals wherein the metalloid is selected from Group IV A of the Periodic Table of Elements; halogen radicals, amido radicals, phosphido radicals, alkoxy radicals, alkylborido radicals or any other radical containing Lewis acidic or basic functionality; or ($C_5H_{4-x}R_x$) is a cyclopentadienyl ring in which at least two adjacent R-groups are joined forming a $C_4$–$C_{20}$ ring to give a saturated or unsaturated polycyclic cyclopentadienyl ligand;

R' is a radical selected from $C_1$–$C_{20}$ aliphatic and alicyclic hydrocarbyl radicals wherein one or more hydrogen atoms may be replaced by radicals selected from halogen, amido, phosphido, alkoxy or any other radical containing a Lewis acidic or basic functionality, with the proviso that R' is covalently bonded to the nitrogen atom through a 1° or 2° carbon atom;

each Q may be independently an univalent anionic ligand, or both Q together may be an alkylidene or a cyclometallated hydrocarbyl or any other divalent anionic chelating ligand with the proviso that where any Q is a hydrocarbyl such Q is not a substituted or unsubstituted cyclopentadienyl radical;

T is a covalent bridging group containing a Group IV A or V A element;

L is a neutral Lewis base; and

"w" is a number from 0 to 3.

2. A compound of the formula:

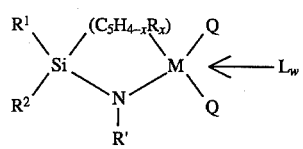

Formula III wherein:

M represents Ti, Hf or Zr;

($C_5H_{4-x}R_x$) is a cyclopentadienyl ring which is substituted with from zero to four substituent groups R, "x" is 0, 1, 2, 3, or 4 denoting the degree of substitution, and each substituent group R is, independently, a radical selected from a group consisting of $C_1$–$C_{20}$ hydrocarbyl radicals, substituted $C_1$–$C_{20}$ hydrocarbyl radicals wherein one or more hydrogen atoms is replaced by a halogen radical, an amido radical, a phosphido radical, and alkoxy radical, $C_1$–$C_{20}$ hydrocarbyl-substituted metalloid radicals wherein the metalloid is selected from Group IV A of the Periodic Table of Elements; halogen radicals, amido radicals, phosphido radicals, alkoxy radicals, alkylborido radicals or any other radical containing Lewis acidic or basic functionality; or ($C_5H_{4-x}R_x$) is a cyclopentadienyl ring in which at least two adjacent R-groups are joined forming a $C_4$–$C_{20}$ ring to give a saturated or unsaturated polycyclic cyclopentadienyl ligand;

each of $R^1$ and $R^2$ are independently selected from $C_1$–$C_{20}$ hydrocarbyl radicals;

each Q is independently selected from halide, hydride, substituted or unsubstituted $C_1$–$C_{20}$ hydrocarbyl radical, alkoxide, aryloxide, amide and phosphide radicals with the proviso that Q is not a substituted or unsubstituted cyclopentadienyl radical;

R' is selected from $C_1$–$C_{20}$ aliphatic and alicyclic hydrocarbyl radicals with the proviso that R' is covalently bonded to the nitrogen atom through a 1° or 2° carbon atom;

L is a neutral Lewis base; and

"w" is a number from 0 to 3.

3. The compound of claim 2 wherein M is Ti.

4. The compound of claim 2 where:

M is Ti; and $R^1$ and $R^2$ are each independently selected from alkyl and aryl radicals having from 1 to 20 carbon atoms.

5. The compound of claim 2 wherein R' is alicyclic.

6. A compound of the formula:

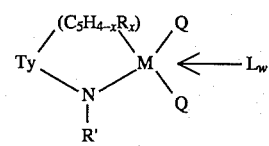

Formula IV

M is Zr, Hf or Ti in its highest formal oxidation state (+4, $d^0$ complex);

($C_5H_{4-x}R_x$) is a cyclopentadienyl ring which is substituted with from zero to four substituent groups R, "x" is 0, 1, 2, 3, or 4 denoting the degree of substitution, and each substituent group R is, independently, a radical selected from a group consisting of $C_1$–$C_{20}$ hydrocarbyl radicals, substituted $C_1$–$C_{20}$ hydrocarbyl radicals wherein one or more hydrogen atoms is replaced by a halogen radical, an amido radical, a phosphido radical, and alkoxy radical, $C_1$–$C_{20}$ hydrocarbyl-substituted metalloid radicals wherein the metalloid is selected from Group IV A of the Periodic Table of Elements; halogen radicals, amido radicals, phosphido radicals, alkoxy radicals, alkylborido radicals or any other radical containing Lewis acidic or basic functionality; or $(C_5H_{4-x}R_x)$ is a cyclopentadienyl ring in which at least two adjacent R-groups are joined forming a $C_4$–$C_{20}$ ring to give a saturated or unsaturated polycyclic cyclopentadienyl ligand;

R' is a radical selected from $C_1$–$C_{20}$ aliphatic and alicyclic hydrocarbyl radicals wherein one or more hydrogen atoms may be replaced by radicals selected from halogen, amido, phosphido, alkoxy or any other radical containing a Lewis acidic or basic functionality, with the proviso that R' is covalently bonded to the nitrogen atom through a 1° or 2° carbon atom;

each Q may be independently an univalent anionic ligand selected from a halide, hydride, or substituted or unsubstituted $C_1$–$C_{20}$ hydrocarbyl, alkoxide, aryloxide, amide, phosphide, or both Q together may be an alkylidene or a cyclometallated hydrocarbyl or any other divalent anionic chelating ligand with the proviso that where any Q is a hydrocarbyl such Q is not a substituted or unsubstituted cyclopentadienyl radical,;

"w" is a number from 0 to 3;

T is selected from radicals of the formula $(CR^3R^4)$ wherein $R^3$ and $R^4$ are independently selected from hydrogen and $C_1$–$C_{20}$ hydrocarbyl radicals; and y is 1 or 2.

7. The compound of claim 6 wherein M is Ti.
8. The compound of claim 6 wherein:
M is Ti and
$R^3$ and $R^4$ are selected from hydrogen, $C_1$–$C_6$ alkyl radicals and $C_6$–$C_{12}$ aryl radicals.
9. A compound of the formula:

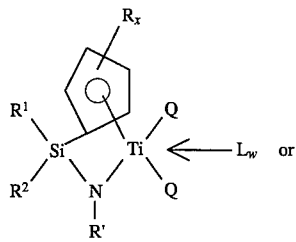

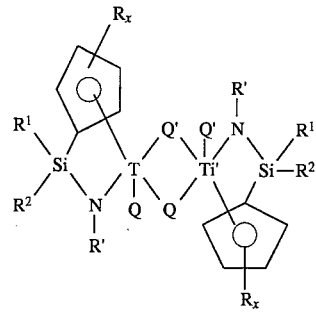

wherein $R^1$ and $R^2$ are each independently a hydrocarbyl radical, each Q and Q' is independently a halide or a $C_1$–$C_{20}$ hydrocarbyl radical, R' is an aliphatic or alicyclic hydrocarbyl radical having from 1 to 20 carbon atoms and R' is covalently bonded to the nitrogen atom through a 1° or 2° carbon atom, L is a neutral Lewis base where "w" denotes a number from 0 to 3 and each R is, independently a $C_1$–$C_4$ hydrocarbyl radical or hydrogen, x is 0, 1, 2, 3 or 4, or two adjacent R groups may join to form a $C_4$–$C_{10}$ ring.

10. The compound of claim 9, having the formula:

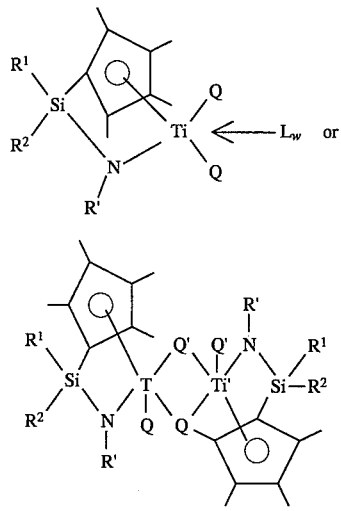

wherein $R^1$ and $R^2$ are each independently a hydrocarbyl radical, each Q and Q' is independently a halide or alkyl radical, R' is an aliphatic or alicyclic hydrocarbyl radical of from 1 to 20 carbon atoms and R' is covalently bonded to the nitrogen atom through a 1° or 2° carbon atom, and L is a neutral Lewis base where "w" denotes a number from 0 to 3.

* * * * *

UNITED STATES PATENT AND TRADEMARK OFFICE
CERTIFICATE OF CORRECTION

PATENT NO. : 5,621,126
DATED : April 15, 1997
INVENTOR(S) : Jo Ann M. Canich

It is certified that error appears in the above-indentified patent and that said Letters Patent is hereby corrected as shown below:

Column 15, lines 42-67; in each occurrence please delete the "1, 1-dimethylethylenetetramethylcyclopentadienyl)" and substitute therfor -- "1, 1-dimethylethylene(tetramethylcyclopentadienyl)" --;

Column 16, lines 35-60; in each occurrence please delete the word "1, 2-dimethylethylenetetramethylcyclopentadienyl)" and substitute therfor -- "1, 2-dimethylethylene(tetramethylcyclopentadienyl)" --;

Column 17, lines 35-60; in each occurrence please delete the word "2, 2-dimethylethylenetetramethylcyclopentadienyl)" and substitute therfor -- "2, 2-dimethylethylene(tetramethylcyclopentadienyl)" --;

Column 21, line 20; please insert a space between the formula "$C_3$" and the word "hydrocarbyl"

Column 21, line 21, please delete the word "hydrocarby" and substitute therefor -- hydrocarbyl --;

UNITED STATES PATENT AND TRADEMARK OFFICE
CERTIFICATE OF CORRECTION

PATENT NO. : 5,621,126
DATED : April 15, 1997
INVENTOR(S) : Jo Ann M. Canich

It is certified that error appears in the above-indentified patent and that said Letters Patent is hereby corrected as shown below:

Column 21, line 28; please delete the formula "CnH2n-1" and substitute therefor -- $C_nH_2n-1$ --;

UNITED STATES PATENT AND TRADEMARK OFFICE
CERTIFICATE OF CORRECTION

PATENT NO. : 5,621,126
DATED : April 15, 1997
INVENTOR(S) : Jo Ann M. Canich

Page 3 of 12

It is certified that error appears in the above-indentified patent and that said Letters Patent is hereby corrected as shown below:

Column 24, lines 30-55; please delete the formulae

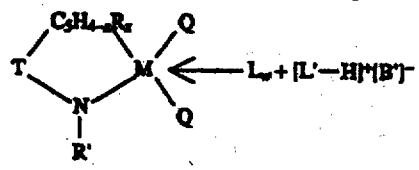

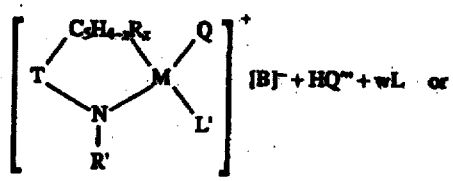

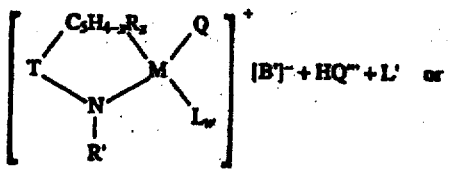

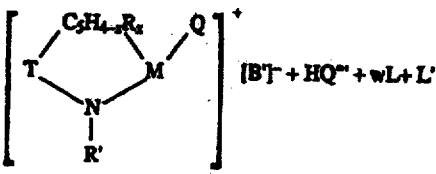

and replaced therefore with

UNITED STATES PATENT AND TRADEMARK OFFICE
CERTIFICATE OF CORRECTION

PATENT NO. : 5,621,126
DATED : April 15, 1997           Page 4 of 12
INVENTOR(S) : Jo Ann M. Canich It is certified that error appears in the above-indentified patent and that said Letters Patent is hereby corrected as shown below:

and replaced therefore with

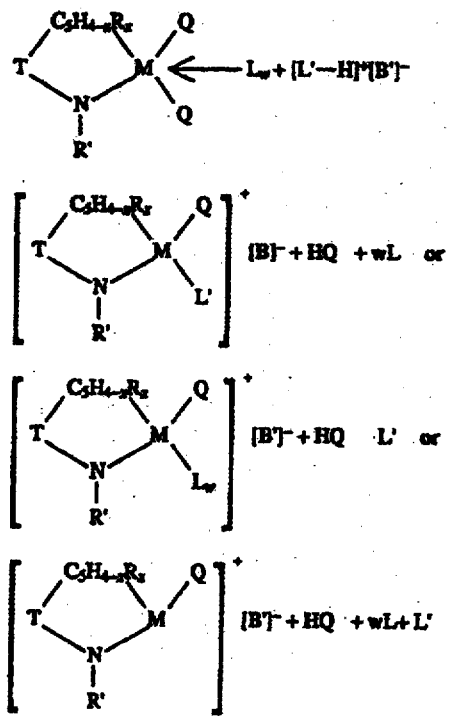

UNITED STATES PATENT AND TRADEMARK OFFICE
CERTIFICATE OF CORRECTION

PATENT NO. : 5,621,126
DATED : April 15, 1997
INVENTOR(S) : Jo Ann M. Canich

Page 5 of 12

It is certified that error appears in the above-indentified patent and that said Letters Patent is hereby corrected as shown below:

Column 26, line 19-26; please delete the formula

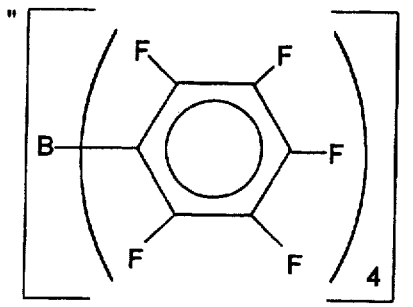

and substitute therefor

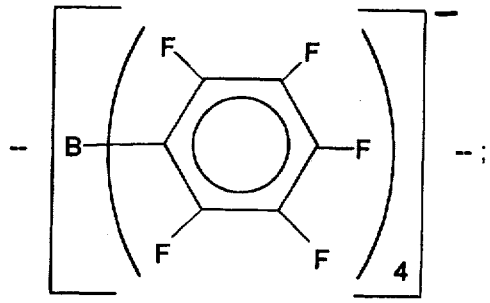

Column 26, line 34; please insert a --.-- after the word "compound";

UNITED STATES PATENT AND TRADEMARK OFFICE
CERTIFICATE OF CORRECTION

PATENT NO. : 5,621,126
DATED : April 15, 1997
INVENTOR(S) : Jo Ann M. Canich

Page 6 of 12

It is certified that error appears in the above-indentified patent and that said Letters Patent is hereby corrected as shown below:

Column 26, lines 39; please delete the phrase "I - V" and substitute therefor the phrase-- I - IV --;

Column 29, line 10; please delete the word "e-olefin" and substitute therefor -- α-olefin --;

Column 29, line 30; please delete the word "e-olefin" and substitute therefor -- α-olefin --;

Column 30, line 41; please delete the word "TlCl$_4$," and substitute therefor therefor -- TiCl$_4$ --;

Column 30, line 42; please delete the word "TlCl$_4$," and substitute therefor therefor -- TiCl$_4$ --;

Column 30, line 44; please delete the word "TiCl$_4 \cdot$2Et$_2$0," and substitute therefor -- "TiCl$_4 \cdot$2Et$_2$0," --;

Column 30, line 62; please delete the expression "53-58" and substitute therefor -- 53-56 --;

UNITED STATES PATENT AND TRADEMARK OFFICE
CERTIFICATE OF CORRECTION

PATENT NO. : 5,621,126
DATED : April 15, 1997
INVENTOR(S) : JoAnn M. Canich

It is certified that error appears in the above-indentified patent and that said Letters Patent is hereby corrected as shown below:

Column 31, line 18; insert a space between the number "1.6" and the letter "M";

Column 31, line 22; delete the word "Li2[MePhSi($C_5Me_4$)(N-t-Bu)]" and substitute therefore -- $Li_2$[MePhSi($C_5Me_4$)(N-t-Bu)]--;

Column 31, line 24; delete the word "$TiCl_4$.$2Et_2O$" and substitute therefore -- $TiCl_4 \cdot 2Et_2O$--;

Column 31, line 53; delete the word "mol" and replace therefore --Mol--;

Column 31, line 53; insert a space between the number "1.4" and the letter "M";

Column 32, line 22; insert a space between the number "1.4" and the letter "M";

Column 32, line 29; delete the word "$TiCl_4$.$2Et_2O$" and substitute therefore -- $TiCl_4 \cdot 2Et_2O$ --;

Column 32, line 55; insert a space between the number "1.4" and the letter "M";

Column 32, line 63; delete the word "$TiCl_4$.$2Et2O$" and substitute therefore -- $TiCl_4 \cdot 2Et_2O$ --;

UNITED STATES PATENT AND TRADEMARK OFFICE
CERTIFICATE OF CORRECTION

PATENT NO. : 5,621,126
DATED : April 15, 1997
INVENTOR(S) : Jo Ann M. Canich

Page 8 of 12

It is certified that error appears in the above-indentified patent and that said Letters Patent is hereby corrected as shown below:

Column 33, line 19; please insert a space between the number "1.4" and the letter "M";

Column 33, line 21; please delete the word "TiCl$_4$.2Et$_2$0" and substitute therefore -- TiCl$_4$•2Et$_2$0 --;

Column 33, line 22; please delete the number "0,030" and substitute therefore the number -- 0.030 --;

Column 33, line 22; please delete the word "TiCl$_4$.2Et$_2$0" and substitute therefore -- TiCl$_4$•2Et$_2$0 --;

Column 33, line 41; please insert a space between the number "1.12" and the letter "M";

Column 33, line 43; please delete the word "TiCl$_4$.2Et$_2$0" and substitute therefore -- TiCl$_4$•2Et$_2$0 --;

Column 33, line 55; please delete the word "(C$_5$Me$_4$H)SiMe$_4$Cl" and substitute therefore -- (C$_5$Me$_4$H)SiMe$_2$Cl --;

Column 33, line 58; please delete the term "Me$_2$Si(C$_5$Me$_4$H(HNC$_8$H$_{17}$)" and substitute therefor the term -- Me$_2$Si(C$_5$Me$_4$H)(HNC$_8$H$_{17}$) --;

Column 33, line 59; please insert a space between the number "2.1" and the letter "M";

Column 33, line 62; please delete the word "TiCl$_4$.2Et$_2$0" and substitute therefore -- TiCl$_4$•2Et$_2$0 --;

Column 34, line 17; please insert a space between the number "1.4" and the letter "M";

Column 34, line 17; please delete one of the two spaces following the number "45";

Column 34, line 17; please delete the term "Ml" and substitute therefor "ml";

UNITED STATES PATENT AND TRADEMARK OFFICE
CERTIFICATE OF CORRECTION

PATENT NO. : 5,621,126
DATED : April 15, 1997
INVENTOR(S) : Jo Ann M. Canich

It is certified that error appears in the above-indentified patent and that said Letters Patent is hereby corrected as shown below:

Column 34, line 19; please delete the word "$TiCl_4.2Et_2O$" and substitute therefore -- $TiCl_4 \cdot 2Et_2O$ --;

Column 34, line 44; please insert a space between the number "1.4" and the letter "M";

Column 34, line 46; please delete the word "$TiCl_4.2Et_2O$" and substitute therefore -- $TiCl_4 \cdot 2Et_2O$ --;

Column 34, line 56; please delete the word "$MephSi(C_5Me_4)(N-s-Bu)TiCl2$" and substitute therefore -- $MePhSi(C_5Me_4)(N-s-Bu)TiCl_2$ --;

Column 34, line 61; please delete the word "$MephSi(C_5Me_4)Cl$" and substitute therefore -- $MePhSi(C_5Me_4H)Cl$ --;

Column 34, line 61; please delete the word "$TiCl_4.2Et_2O$" and substitute therefore -- $TiCl_4 \cdot 2Et_2O$ --;

Column 35, line 4; please insert a space between the number "1.4" and the letter "M";

Column 35, line 6; please delete the word "$TiCl_4.2Et_2O$" and substitute therefore -- $TiCl_4 \cdot 2Et_2O$ --;

Column 35, line 25; please delete the term "LiHn-s-Bu" and substitute therefor -- "LiHN-s-Bu" --;

Column 35, line 33; please insert a space between the number "1.4" and the letter "M";

Column 35, line 40; please delete the word "$TiCl_4.2Et_2O$" and substitute therefore -- $TiCl_4 \cdot 2Et_2O$ --;

Column 35, line 65; please insert a space between the number "1.4" and the letter "M";

UNITED STATES PATENT AND TRADEMARK OFFICE
CERTIFICATE OF CORRECTION

PATENT NO. : 5,621,126
DATED : April 15, 1997
INVENTOR(S) : Jo Ann M. Canich

It is certified that error appears in the above-indentified patent and that said Letters Patent is hereby corrected as shown below:

Column 36, line 4; please delete the word "$TiCl_4.2Et_2O$" and substitute therefore -- $TiCl_4 \cdot 2Et_2O$ --;

Column 36, line 38; please delete the word "$Me_2Si(MeC5H4)(HNC12H23)$" and substitute therefore -- $Me_2Si(MeC_5H_4)(HNC_{12}H_{23})$ --;

Column 36, line 39; please insert a space between the number "1.4" and the letter "M";

Column 36, line 45; please delete the word "$TiCl_4.2Et_2O$" and substitute therefore -- $TiCl_4 \cdot 2Et_2O$ --;

Column 37, line 7; please insert a space between the number "1.4" and the letter "M";

Column 37, line 13; please delete the word "$TiCl_4.2Et_2O$" and substitute therefore -- $TiCl_4 \cdot 2Et_2O$ --;

Column 37, line 28; please insert a space between the number "1.4" and the letter "M";

Column 37, line 45; please insert a space between the number "1.0" and the letter "M";

Column 37, line 45; please delete the number "0,206" and substitute therefore the number -- 0.206 --;

Column 37, line 53; please delete the number "2,676" and substitute therefore the number -- 2.676 --;

Column 37, line 59; please insert a space between the number "1.0" and the letter "M";

Column 38, line 6; please insert a space between the number "1.0" and the letter "M";

Column 38, line 20; please insert a space between the number "1.0" and the letter "M";

UNITED STATES PATENT AND TRADEMARK OFFICE
CERTIFICATE OF CORRECTION

PATENT NO. : 5,621,126
DATED : April 15, 1997
INVENTOR(S) : Jo Ann M. Canich

It is certified that error appears in the above-indentified patent and that said Letters Patent is hereby corrected as shown below:

Column 38, line 35; please insert a space between the number "1.4" and the letter "M";

Column 39, line 5; please insert a space between the number "1.0" and the letter "M";

Column 39, line 32; please insert a space between the number "1.0" and the letter "M";

Column 38, line 43; please delete the number "2,579," and substitute the number -- 2.579, --;

Column 38, line 49; please insert a space between the number "1.0" and the letter "M";

Column 38, line 63; please insert a space between the number "1.0" and the letter "M";

Column 39, line 10; please insert a space between the number "1.0" and the letter "M";

Column 39, line 33; please insert a space between the number "1.0" and the letter "M";

UNITED STATES PATENT AND TRADEMARK OFFICE
CERTIFICATE OF CORRECTION

PATENT NO. : 5,621,126
DATED : April 15, 1997
INVENTOR(S) : Jo Ann M. Canich

It is certified that error appears in the above-indentified patent and that said Letters Patent is hereby corrected as shown below:

Column 44, "Table 1"; please delete "Table 1" and replace with --

TABLE 1

| Ex. # | TMC (g) | MAO (L) | Total Vol (L) | TMC (g/L) | MAO (g/L) | Feed Rate (L/hr) | Production Rate (kg/hr) | A/M | TMC Productivity (kg/g) | Catalyst Productivity (kg/g) | MW | MWD | MI | Wt % C4 | Method | rl |
|---|---|---|---|---|---|---|---|---|---|---|---|---|---|---|---|---|
| JT | 71 | 0.540 | 0.4 | 10 | 0.0540 | 10.4 | 1.75 | 5.1 | 1595 | 54 | 0.28 | 63,600 | 2.363 | 11.3 | 42.0 | 1HMMR | 4.4 |
| KT | 72 | 2.259 | 1.8 | 6 | 0.3765 | 78.3 | 0.51 | 3.9 | 1723 | 20 | 0.10 | 84,100 | 4.775 | 3.3 | 40.8 | 1HMMR | 4.7 |
| LT | 73 | 1.480 | 1.2 | 8 | 0.1850 | 39.2 | 0.46 | 4.0 | 1541 | 48 | 0.22 | 72,700 | 3.610 | 7.9 | 42.0 | 1HMMR | 4.4 |
| MT | 74 | 1.366 | 1.0 | 6 | 0.2277 | 43.5 | 0.58 | 4.0 | 1398 | 31 | 0.16 | 78,300 | 4.601 | 5.0 | 40.8 | 1HMMR | 4.7 |
| PT | 75 | 0.859 | 0.6 | 5.3 | 0.1620 | 29.5 | 1.14 | 4.2 | 1239 | 23 | 0.12 | 61,400 | 2.607 | 13.2 | 41.9 | 13CMMR | 4.4 |
| NT | 76 | 1.441 | 1.2 | 8 | 0.1801 | 39.2 | 1.51 | 4.4 | 1485 | 16 | 0.07 | 85,400 | 3.971 | 3.6 | 44.0 | 1HMMR | 4.1 |
| AT | 77 | 0.888 | 0.7 | 5 | 0.1776 | 35.0 | 0.56 | 4.35 | 1461 | 44 | 0.22 | 50,200 | 2.360 | 19 | 24.0 | 13CMMR | 10 |
| OT | 78 | 1.934 | 1.3 | 6 | 0.3223 | 54.4 | 0.62 | 4.3 | 1252 | 22 | 0.13 | 64,600 | 2.494 | 8.1 | 43.6 | 13CMMR | 4.1 |
| PT | 79 | 1.900 | 1.3 | 6 | 0.3167 | 54.4 | 0.96 | 3.75 | 1274 | 12 | 0.07 | 71,200 | 2.259 | 3.8 | 41.1 | 13CMMR | 4.6 |
| IT | 80 | 0.878 | 0.8 | 10 | 0.0878 | 19.6 | 0.84 | 4.3 | 1416 | 59 | 0.26 | 63,600 | 2.751 | 6.6 | 32.4 | 1HMMR | 6.7 |
| QT | 81 | 0.953 | 0.9 | 10 | 0.0953 | 23.5 | 1.32 | 4.9 | 1565 | 39 | 0.16 | 64,500 | 2.342 | 10 | 42.8 | 1HMMR | 4.3 |
| RT | 82 | 0.885 | 0.9 | 10 | 0.0885 | 23.5 | 1.68 | 4.65 | 1685 | 31 | 0.12 | 71,100 | 2.262 | 8.8 | 40.0 | 1HMMR | 4.8 |
| JT | 83 | 1.494 | 0.5 | 10 | 0.1494 | 13.1 | 1.02 | 3.9 | 721 | 26 | 0.29 | 78,200 | 2.617 | 5.2 | 40.8 | 1HMMR | 4.6 |
| ST | 84 | 3.053 | 1.0 | 12 | 0.2540 | 21.8 | 0.51 | 2.9 | 643 | 22 | 0.26 | 60,500 | 2.183 | 8.5 | 17.62 | 13CMMR | 15.0 |
| TT | 85 | 3.043 | 1.0 | 18 | 0.1690 | 14.5 | 1.11 | 2.6 | 708 | 14 | 0.16 | 53,900 | 2.308 | 13.8 | 17.38 | 13CMMR | 15.2 |
| UT | 86 | 1.566 | 1.0 | 5 | 0.3132 | 52.2 | 0.35 | 5.0 | 1258 | 46 | 0.27 | 70,200 | 2.441 | 4.6 | 46.4 | 13CMMR | 3.7 |

Signed and Sealed this

Fifth Day of September, 2000

Attest:

Q. TODD DICKINSON

Attesting Officer

*Director of Patents and Trademarks*